(12) United States Patent
Umakoshi et al.

(10) Patent No.: US 8,765,952 B2
(45) Date of Patent: Jul. 1, 2014

(54) METAL COMPLEX, LIGHT EMITTING ELEMENT, AND DISPLAY DEVICE

(75) Inventors: Keisuke Umakoshi, Nagasaki (JP); Ami Higashitani, Nagasaki (JP); Kazutoyo Kimura, Nagasaki (JP); Shoji Ishizaka, Hokkaido (JP); Noboru Kitamura, Hokkaido (JP)

(73) Assignee: Nagasaki University, Nagasaki (JP)

( * ) Notice: Subject to any disclaimer, the term of this patent is extended or adjusted under 35 U.S.C. 154(b) by 0 days.

(21) Appl. No.: 13/825,269

(22) PCT Filed: Sep. 15, 2011

(86) PCT No.: PCT/JP2011/071156
§ 371 (c)(1),
(2), (4) Date: Jun. 3, 2013

(87) PCT Pub. No.: WO2012/039347
PCT Pub. Date: Mar. 29, 2012

(65) Prior Publication Data
US 2013/0253189 A1 Sep. 26, 2013

(30) Foreign Application Priority Data

Sep. 21, 2010 (JP) ................................. 2010-211191
Mar. 10, 2011 (JP) ................................. 2011-053216

(51) Int. Cl.
*C07F 15/00* (2006.01)
*H01L 51/50* (2006.01)

(52) U.S. Cl.
USPC .................. 546/2; 313/504; 546/10; 544/225

(58) Field of Classification Search
USPC ........................... 546/2, 10; 313/504; 544/225
See application file for complete search history.

(56) References Cited

U.S. PATENT DOCUMENTS

| 7,973,167 B2 * | 7/2011 | Umakoshi et al. ............ 548/101 |
| 2006/0216542 A1 | 9/2006 | Wu |
| 2007/0270592 A1 | 11/2007 | Ragini et al. |
| 2009/0198069 A1 | 8/2009 | Umakoshi et al. |
| 2010/0105918 A1 | 4/2010 | Umakoshi et al. |
| 2010/0311982 A1 | 12/2010 | Umakoshi et al. |

FOREIGN PATENT DOCUMENTS

| JP | 2005-259377 A | 9/2005 |
| JP | 2007-308499 A | 11/2007 |
| JP | 2008-081401 A | 4/2008 |
| JP | 2009-215277 A | 9/2009 |
| WO | WO 2008/108407 A1 | 9/2008 |
| WO | WO 2009/101966 A1 | 8/2009 |

OTHER PUBLICATIONS

Bandini et al., *Canadian Journal of Chemistry*, 57: 3237-3242 (1979).
Umakoshi et al., *60$^{th}$ JSCC Symposium and 60$^{th}$ Anniversary Conference on Coordination Chemistry*, Osaka, Japan, p. 162, item 3lc-10 (2010).
Umakoshi et al., *Bulletin of the Chemical Society of Japan*, 83(12): 1504-1510 (2010).
Yu et al., *Chinese Journal of Inorganic Chemistry*, 22 (5): 941-944 (2006).
Japanese Patent Office, International Search Report in International Patent Application No. PCT/JP2011/071156 (Oct. 25, 2011).

* cited by examiner

*Primary Examiner* — Charanjit Aulakh
(74) *Attorney, Agent, or Firm* — Leydig, Voit & Mayer, Ltd.

(57) ABSTRACT

The present invention provides a metal complex containing a cation represented by $[(M^{II})_2(M^{I})_2(L_C)_2(L_B)_4]^{2+}$ [in the aforementioned formula, $M^{II}$ is $Pt^{II}$ or $Pd^{II}$, $M^{I}$ is $H^+$, $Au^I$, $Ag^I$, $Cu^I$, $Hg^I$, $Tl^I$ or $Pb^I$, and $L_C$ and $L_B$ are ligands]. The metal complex of the present invention is useful as a light emitting material of an organic EL device.

18 Claims, 13 Drawing Sheets

Emission spectra (solid state)

Absorption spectrum (CH$_3$CN)

Emission spectrum (Solid state)

Absorption spectrum (CH$_3$CN)

Emission spectrum (Solid state)

Emission spectra(solid state)

Absorption spectra (in $CH_3CN$)

Emission spectrum ( solid state)

Absorption spectra (in $CH_3CN$)

Emission spectrum (solid state)

Absorption spectra (in CH₃CN)

Emission spectrum (solid state)

Absorption spectra (in $CH_3CN$)

Emission spectrum (solid state)

Emission spectrum (solid state)

Emission spectrum (solid state)

Emission spectrum (solid state)

Emission spectrum (solid state)

yellow emission

Emission spectrum (solid state)

blue emission

Emission spectrum (solid state)

METAL COMPLEX, LIGHT EMITTING ELEMENT, AND DISPLAY DEVICE

CROSS-REFERENCE TO RELATED APPLICATIONS

This patent application is the U.S. national phase of International Patent Application No. PCT/JP2011/071156, filed on Sep. 15, 2011, which claims the benefit of Japanese Patent Application No. 2011-053216, filed Mar. 10, 2011, and Japanese Patent Application No. 2010-211191, filed Sep. 21, 2010, which are incorporated by reference in their entireties herein.

TECHNICAL FIELD

The present invention relates to a metal complex showing luminescence. In addition, the present invention also provides a light emitting device and a display device containing the aforementioned metal complex.

BACKGROUND ART

In an organic EL (electroluminescence) device for display devices, emission from a singlet excited state (that is, fluorescence) has been conventionally utilized. In this case, maximum emission efficiency is 25%, and therefore, the emission efficiency is extremely low. As a method of increasing emission efficiency, therefore, utilization of emission from triplet excited state (that is, phosphorescence) has been proposed. When phosphorescence is utilized, the emission efficiency may be 100% in theory.

In addition, a metal complex wherein iridium is cyclometallized with phenylpyridine has been reported to generate phosphorescence at high efficiency even at room temperature. Since then, the study of phosphorescent light emitting materials has been mostly focused on iridium complex as a target, and therefore, the possibility of other metal complexes as a light emitting device has not been sufficiently evaluated yet.

The present inventors tried to synthesize a mixed metal complex by using 3,5-dimethylpyrazole, and succeeded in isolation of a metal complex showing very strong emission on irradiation of UV light. As a result of the measurement of emission from this metal complex, it was found that a mixed metal complex containing platinum and silver exhibited phosphorescent blue emission, and the emission quantum yield in a solid state and a solution was higher than that of a phenylpyridine-iridium complex and 0.85 and 0.51, respectively. The emission properties of this metal complex are not inferior to that of a material having the best emission properties among the compounds known to date as the light emitting materials of organic EL devices.

Moreover, the present inventors have heretofore synthesized a series of mixed metal complexes by using pyrazole having various substituents, and developed some metal complexes having a high solid-state emission quantum yield (see, for example, patent document 1). However, sufficient EL properties have not yet been obtained from conventional metal complexes.

DOCUMENT LIST

Patent Document patent document 1: JP-A-2008-81401

SUMMARY OF THE INVENTION

Problems to be Solved by the Invention

The reason why sufficient EL properties have not yet been obtained from conventional metal complexes is considered to be that potential emission properties of the light emitting materials thereof cannot be sufficiently exhibited as EL properties, since the absorption bands of conventional metal complexes are located on the short wavelength side, and conventional metal complexes require high excitation energy.

The present invention has been made in view of such situation, and aims to provide a metal complex having the absorption bands shifted toward the long wavelength side than that (about 250-350 nm) of conventional mixed metal complexes bridged by pyrazolate, which shows sufficient EL properties when used as a light emitting material of an organic EL device.

Means of Solving the Problems

The present inventors have conducted intensive studies in an attempt to solve the aforementioned problem and found that a metal complex containing cation represented by the following formula (C1) has absorption bands shifted toward the long wavelength side than in conventional products, and can be excited with lower energy. The present invention based on this finding is as follows.

[1] A metal complex containing a cation represented by the formula (C1)

$$[(M^{II})_2(M^{I})_2(L_C)_2(L_B)_4]^{2+} \quad (C1)$$

in the formula (C1), $M^{II}$ is $Pt^{II}$ or $Pd^{II}$, $M^{I}$ is $H^+$, $Au^{I}$, $Ag^{I}$, $Cu^{I}$, $Hg^{I}$, $Tl^{I}$ or $Pb^{I}$, $L_C$ is a compound represented by any of the formula ($L_C$-1)- the formula ($L_C$-5), and $L_B$ is a monovalent anion represented by the formula ($L_B$-1).

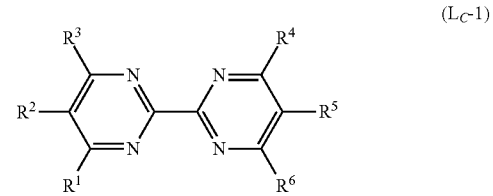

($L_C$-1)

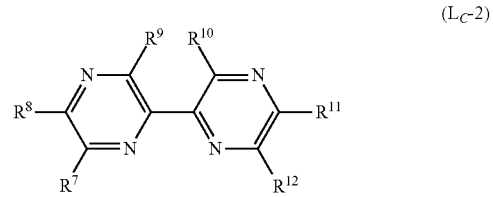

($L_C$-2)

-continued

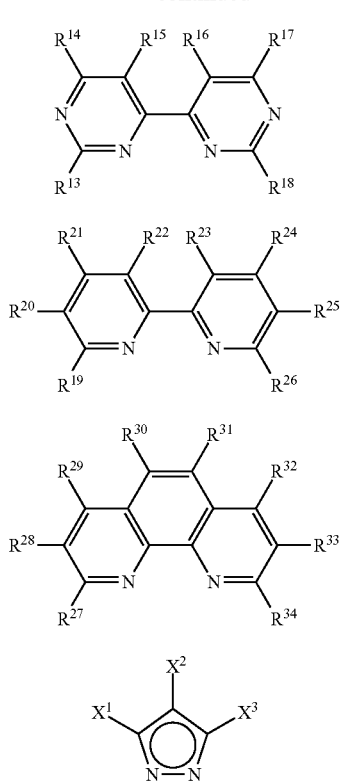

(L$_C$-3)

(L$_C$-4)

(L$_C$-5)

(L$_B$-1)

in the formula (L$_C$-1)-the formula (L$_C$-5), R$^1$-R$^{34}$ are each independently a hydrogen atom, a halogen atom, an alkyl group optionally having substituent(s), or an aryl group optionally having substituent(s), or one or plural sets of the adjacent groups from R$^1$-R$^{34}$ form a hydrocarbon ring optionally having substituent(s) or a heterocyclic ring optionally having substituent (s), in the formula (L$_B$-1), X$^1$ is an alkyl group optionally having substituent(s), and X$^2$ and X$^3$ are each independently a hydrogen atom, a halogen atom, an alkyl group optionally having substituent(s), or an aryl group optionally having substituent(s).

[2] The metal complex of the above-mentioned [1], which is represented by the formula (C2)

$$[(M^{II})_2(M^I)_2(L_C)_2(L_B)_4](PF_6)_2 \quad (C2)$$

in the formula (C2), M$^{II}$, M$^I$, L$_C$ and L$_B$ are as defined above.

[3] The metal complex of the above-mentioned [1] or [2], wherein M$^{II}$ is Pt$^{II}$, M$^I$ is H$^+$, Au$^I$, Ag$^I$ or Cu$^I$, L$_C$ is 2,2'-bipyrimidine or 2,2'-bipyridine (preferably 2,2'-bipyridine), and L$_B$ is a monovalent anion obtained by dissociation of a proton from 3-t-butylpyrazole.

[4] The metal complex of the above-mentioned [1] or [2], wherein M$^{II}$ is Pt$^{II}$, M$^I$ is H$^+$ or Ag$^I$, L$_C$ is 4,4'-dimethyl-2,2'-bipyridine or 5,5'-dimethyl-2,2'-bipyridine (preferably 4,4'-dimethyl-2,2'-bipyridine), and L$_B$ is a monovalent anion obtained by dissociation of a proton from 3-t-butylpyrazole.

[5] A light emitting device having a light emitting layer containing the metal complex of any one of the above-mentioned [1]-[4].

[6] A display device provided with the light emitting device of the above-mentioned [5].

In the following, "a compound represented by the formula (L$_C$-1)" is sometimes abbreviated as "compound (L$_C$-1)".

Compounds, anions, cations and metal complexes, which are represented by other formulas, are also sometimes abbreviated in the same manner.

Effect of the Invention

According to the aforementioned metal complex of the present invention, sufficient EL properties can be afforded when it is used as a light emitting material of an organic EL device. In addition, by using this metal complex of the present invention, a novel light emitting device and a novel display device can be provided.

DESCRIPTION OF EMBODIMENTS

Figure 1:
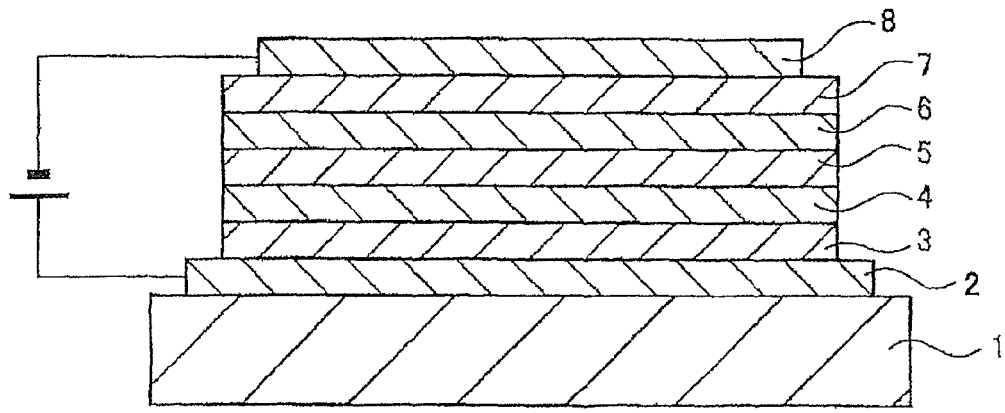
FIG. 1 is a cross-sectional view showing an example of a light emitting device of the present invention.

A mode for carrying out the present invention will be described below.

The metal complex of the present invention is a metal complex containing the cation represented by the formula (C1).

$$[(M^{II})_2(M^I)_2(L_C)_2(L_B)_4]^{2+} \quad (C1)$$

That is, the metal complex of the present invention is a polynuclear metal complex constituted of two kinds of cations $M^{II}$ and $M^I$ (metal ion or H$^+$), chelating ligand $L_C$, and crosslinking ligand $L_B$.

$M^{II}$ is Pt$^{II}$ or Pd$^{II}$, preferably Pt$^{II}$.

$M^I$ is H$^+$, Au$^I$, Ag$^I$, Cu$^I$, Hg$^I$, Tl$^I$ or Pb$^I$, preferably H$^+$, Au$^I$, Ag$^I$ or Cu$^I$, more preferably Ag$^I$.

$L_C$ is a compound represented by any of the aforementioned formula (L$_C$-1)-the formula (L$_C$-5). Here, compound (L$_C$-1) is 2,2'-bipyrimidine optionally having substituent(s), compound (L$_C$-2) is 2,2'-bipyrazine optionally having substituent(s), compound (L$_C$-3) is 4,4'-bipyrimidine optionally having substituent(s), compound (L$_C$-4) is 2,2'-bipyridine optionally having substituent(s), and compound (L$_C$-5) is 1,10-phenanthrolin optionally having substituent(s).

$R^1$-$R^{34}$ in the aforementioned formula (L$_C$-1)-the formula (L$_C$-5) are each independently a hydrogen atom, a halogen atom, an alkyl group optionally having substituent(s), or an aryl group optionally having substituent(s), or one or plural sets of the adjacent groups from $R^1$-$R^{34}$ form a hydrocarbon ring optionally having substituent(s) or a heterocyclic ring optionally having substituent(s). $R^1$-$R^{34}$ are each independently preferably a hydrogen atom, a halogen atom or an alkyl group optionally having substituent(s), more preferably a hydrogen atom or an alkyl group.

Examples of the halogen atom include a fluorine atom, a chlorine atom, a bromine atom, an iodine atom and the like.

The alkyl group may be any of linear, branched and cyclic. Examples of the substituent that the alkyl group can have include the aforementioned halogen atom and the like.

Examples of the alkyl group optionally having substituent(s) include a methyl group, an ethyl group, a propyl group, an i-propyl group, a butyl group, an i-butyl group, a t-butyl group, a pentyl group, a hexyl group, a cyclohexyl group, a heptyl group, an octyl group, an ethylhexyl group, a trifluoromethyl group, a pentafluoroethyl group, a perfluorobutyl group, a perfluorohexyl group and the like. The alkyl group for $R^1$-$R^{34}$ preferably has 1-8, more preferably 1-4, carbon atoms.

The aryl group may be any of an aromatic hydrocarbon group (e.g., a phenyl group, a naphthyl group, an anthryl group) and a heterocyclic aromatic hydrocarbon group (e.g., a pyridyl group), preferably an aromatic hydrocarbon group. The aryl group for $R^1$-$R^{34}$ is preferably 6- to 14-membered, more preferably 6- to 10-membered. Examples of the substituent that the aryl group can have include the aforementioned halogen atom, an alkyl group optionally having substituent(s) and the like.

Examples of the aforementioned hydrocarbon ring formed by the adjacent $R^1$-$R^{34}$ include ring A represented by the formula (1).

(1)

The aforementioned hydrocarbon ring or the aforementioned heterocyclic ring formed by the adjacent $R^1$-$R^{34}$ may be an aromatic ring or a nonaromatic ring, or may have substituent(s). Examples of the aforementioned hydrocarbon ring include a benzene ring, an alicyclic hydrocarbon ring and the like. Examples of the aforementioned heterocyclic ring include an imidazole ring, a pyrazine ring, a quinoxaline ring and the like. The aforementioned hydrocarbon ring or the aforementioned heterocyclic ring formed by the adjacent $R^1$-$R^{34}$ may be a ring formed by plural fused rings, or a ring formed by plural rings bonded by a single bond etc. and the like. Examples of the substituent that the aforementioned hydrocarbon ring or the aforementioned heterocyclic ring can have include the aforementioned halogen atom, an alkyl group optionally having substituent(s), an aryl group optionally having substituent(s) and the like.

$L_C$ is preferably compound (L$_C$-1) or compound (L$_C$-4). Of compound (L$_C$-1), 2,2'-bipyrimidine ($R^1$-$R^6$: hydrogen atom) and 5,5'-dimethyl-2,2'-bipyrimidine ($R^2$ and $R^5$: methyl group; $R^1$, $R^3$, $R^4$ and $R^6$: hydrogen atom) are preferable, and 2,2'-bipyrimidine is more preferable. Of the compounds of the formula (L$_C$-4), 2,2'-bipyridine ($R^{19}$-$R^{26}$: hydrogen atom), 4,4'-dimethyl-2,2'-bipyridine ($R^{21}$ and $R^{24}$: methyl group; $R^{19}$, $R^{20}$, $R^{22}$, $R^{23}$, $R^{25}$ and $R^{26}$: hydrogen atom) and 5,5'-dimethyl-2,2'-bipyridine ($R^{20}$ and $R^{25}$: methyl group; $R^{19}$, $R^{21}$-$R^{24}$ and $R^{26}$: hydrogen atom) are preferable, 2,2'-bipyridine and 4,4'-dimethyl-2,2'-bipyridine are more preferable, and 2,2'-bipyridine is particularly preferable.

$L_B$ is a monovalent anion represented by the aforementioned formula (L$_B$-1). In detail, $L_B$ is a monovalent anion obtained by dissociating a proton from a compound represented by the formula (L$_B$-2).

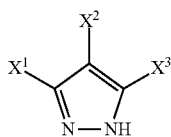

(L_B-2)

In the aforementioned formula (L_B-1) and the aforementioned formula (L_B-2), $X^1$ is an alkyl group optionally having substituent(s), and $X^2$ and $X^3$ are each independently a hydrogen atom, a halogen atom, an alkyl group optionally having substituent(s), or an aryl group optionally having substituent(s). Examples of the halogen atom, the alkyl group optionally having substituent(s), and the aryl group optionally having substituent(s) for $X^1$, $X^2$ or $X^3$ include those mentioned above.

The alkyl group for $X^1$ preferably has 1-8, more preferably 1-4, carbon atoms. $X^1$ is more preferably a butyl group optionally having substituent(s), particularly preferably a t-butyl group.

The alkyl group for $X^2$ or $X^3$ each independently preferably has 1-4 carbon atoms, and the aryl group for $X^2$ or $X^3$ is preferably 6- to 14-membered, more preferably 6- to 10-membered. Preferably, $X^2$ and $X^3$ are each independently a hydrogen atom, a halogen atom or an alkyl group optionally having substituent(s), more preferably a hydrogen atom, a halogen atom or a methyl group, further preferably a hydrogen atom. Particularly preferably, $L_B$ is a monovalent anion obtained by dissociating a proton from 3-t-butylpyrazole.

The metal complex of the present invention contains a counter anion in addition to cation (C1). As the counter anion, those known in the field of the metal complex can be used. Examples of the counter anion include halide ion, pseudohalide ion, hexafluorophosphate ion, tetrafluoroborate ion, tetraphenylborate ion, perchlorate ion, nitrate ion, sulfate ion, carbonate ion, phosphate ion, nitrite ion and the like. Among these, tetrafluoroborate ion ($BF_4$—) and hexafluorophosphate ion ($PF_6$—) are preferable, since a stable complex can be obtained, and $PF_6$— is more preferable. That is, a more preferable metal complex of the present invention is represented by the formula (C2):

(C2)

in the formula (C2), $M^{II}$, $M^I$, $L_C$ and $L_B$ are as defined above.

In the next part, the synthesis of the metal complex of the present invention is described. The metal complex of the present invention can be synthesized using compound ($L_C$-1)-compound ($L_C$-5) (hereinafter these are sometimes to be collectively abbreviated as "compound ($L_C$-1) and the like") and compound ($L_B$-2) as starting materials.

As compound ($L_C$-1) and the like, commercially available compounds can be used. In addition, compound ($L_C$-1) and the like can be synthesized by a known method (e.g., the method described in Inorg. Chem., 46, 2432-2445 (2007), etc.) or by a combination of known methods.

As compound ($L_B$-2), a commercially available compound can be used. In addition, compound ($L_B$-2) can be synthesized by a known method or by a combination of known methods. For example, compound ($L_B$-2) can be synthesized by the following method. First, an intermediate diketone compound can be obtained by the method described in J. Am. Chem. Soc., 72, 1352-1356 (1950). Next, this diketone compound is reacted with hydrazine or hydrazine monohydrate by the methods described in Bull. Soc. Chim., 45, 877-884 (1929), Chem. Abstr., 24, 7541 (1930), Tetrahedron, 42, 15, 4253-4257 (1986), Heterocycles, 53, 1285 (2000) and the like to give compound ($L_B$-2).

A desired diketone compound can be synthesized by a method other than the aforementioned synthesis methods. For example, the compound can also be synthesized by an oxidation reaction of β-unsaturated ketone or by a reaction of ketocarboxylic acid with a Grignard reagent of alkyl bromide.

In addition, compound ($L_B$-2) can also be synthesized by, is without limitation to the aforementioned method using a diketone compound as a starting material, the methods described in J. Heterocyclic Chem., 35, 1377 (1998), Organic Syntheses, 39, 27-30 (1959), J. Heterocyclic Chem., 21(4), 937-943 (1984), J. Am. Chem. Soc., 79, 5242-5245 (1957), J. Heterocyclic Chem., 24(1), 117-119 (1981), J. Medicinal Chemistry, 24(1), 117-119 (1981), J. Medicinal Chemistry, 20(6), 847-850 (1977), J. Heterocyclic Chem., 21(4), 937-943 (1984), J. Chem. Soc., Perkin Transactions 1, (23), 2901-2907 (1973), or methods analogous thereto.

One embodiment of the synthesis method of the metal complex of the present invention, which uses compound ($L_C$-1) and the like and compound ($L_B$-2), is now explained. First, a mononuclear complex $[M^{II}(L_C)(L_BH)_2](PF_6)_2$ is synthesized as an intermediate product. As a specific example, a mononuclear complex $[Pt(bpym)(3\text{-}{}^tBupzH)_2](PF_6)_2$ obtained by reacting a platinum complex $[PtCl_2(bpym)]$ with 3-${}^t$BupzH can be mentioned. Here, bpym is 2,2'-bipyrimidine and 3-${}^t$BupzH is 3-t-butylpyrazole. Then, this mononuclear complex $[M^{II}(L_C)(L_BH)_2](PF_6)_2$ is reacted with a base or a compound of $M^I$ to give a metal complex represented by the formula (C2), i.e., $[(M)_2(M^I)_2(L_C)_2(L_B)_4](PF_6)_2$. A metal complex containing cation (C1) and counter anions other than hexafluorophosphate ions ($PF_6^-$) can be obtained by exchanging $PF_6^-$ of the metal complex (C2) with other counter anions by a known method, and the like.

The synthesis method of the metal complex of the present invention is not limited to the aforementioned methods and the metal complex may be synthesized by other methods.

In the next part, the use of the metal complex of the present invention will be described below. The metal complex of the present invention can be used as a luminescent agent contained in a light emitting layer of a light emitting device such as an organic EL device and the like. Furthermore, the metal complex of the present invention can also be used as an agent for hole injection layer/hole transport layer, and an agent for electron injection layer/electron transport layer. In addition, the metal complex of the present invention can be used as a sensor for organic molecule or gas molecule and the like, an antitumor drug, or a material of a luminescent paint and the like. The use of the metal complex of the present invention is not limited thereto.

Next, a light emitting device whose light emitting layer includes such a metal complex will be described below. FIG. 1 is a cross-sectional view showing an example of a light emitting device of the present invention. The light emitting device shown in FIG. 1 has a constitution wherein an anode 2 is formed on a transparent substrate 1 such as glass and the like, a hole injection layer 3, a hole transport layer 4, a light emitting layer 5, an electron transport layer 6 and an electron injection layer 7 are laminated on the anode 2, and further, a cathode 8 is formed on the electron injection layer 7. That is, it is a five-layer light emitting device having five layers of the hole injection layer 3, the hole transport layer 4, the light emitting layer 5, the electron transport layer 6 and the electron injection layer 7 formed by lamination between the anode 2 and the cathode 8.

The light emitting device of the present invention is not limited to the aforementioned five-layer light emitting device. Alternatively, the light emitting device may be a four-layer light emitting device in which the electron transport layer is omitted from the five-layer light emitting device. The light emitting device may also be a three-layer light emitting device in which the hole injection layer and the electron injection layer are omitted from the five-layer light emitting device. The light emitting device may also be a two-layer light emitting device having one layer used as both a light emitting layer and an electron transport layer of the three-layer light emitting device. The light emitting device may also be a single-layer light emitting device having only a light emitting layer formed between an anode and a cathode.

The light emitting layer of the light emitting device of the present invention may contain the metal complex of the present invention as a guest luminescent agent or as a host luminescent agent. When the metal complex of the present invention is used as a guest luminescent agent, examples of the host luminescent agent to be combined therewith include a metal complex having 8-quinolinol as a ligand such as tris(8-hydroxyquinolinato)aluminum; a carbazole derivative such as CBP (4,4'-N,N'-dicarbazolebiphenyl); dicyanomethylene (DCM); coumarin; perylene; rubrene and the like.

An operation of a light emitting device of the present invention essentially includes a process of injecting electrons and holes from electrodes, a process of transferring the electrons and the holes in a solid, a process of recombining the electrons with the holes to produce a triplet exciton, and a process of allowing the exciton to emit light. These processes are essentially not different between a single-layer light emitting device and a stacked light emitting device. In the single-layer light emitting device, however, characteristics of the four processes can be improved only by changing the molecular structure of the luminescent agent, whereas in the stacked light emitting device, the functions required for each process can be shared by a plurality of materials and each material can be optimized independently. Generally, therefore, a desired performance can be more easily achieved by forming a stacked light emitting device than by forming a single-layer light emitting device.

The light emitting device of the present invention may be used in a display device. Hence, the present invention also provides a display device provided with the aforementioned light emitting device. The display device of the present invention contains the metal complex of the present invention in a light emitting layer of the light emitting device.

The present invention is not limited to the aforementioned mode for carrying out the present invention. Obviously, various other embodiments can be provided without departing from the gist of the present invention.

EXAMPLES

Examples of the present invention will be specifically described below. However, the present invention is not limited to these examples.

Example 1

$[Pt_2(bpym)_2(3\text{-}^tBupz)_2(3\text{-}^tBupzH)_2](PF_6)_2$ which is an example of the metal complex of the present invention was synthesized. This metal complex has a constitution wherein, in the above-mentioned formula (C1), $M^{II}$ is $Pt^{II}$, $M^I$ is $H^+$, $L_C$ is bpym, $L_B$ is 3-$^t$Bupz, and the counter anion is $PF_6^-$. Two $H^+$ and two 3-$^t$Bupz are bonded to form two 3-$^t$BupzH. 3-$^t$Bupz is a monovalent anion obtained by dissociating a proton from the N atom of 3-t-butylpyrazole (3-$^t$BupzH).

First, a mononuclear complex $[Pt(bpym)(3\text{-}^tBupzH)_2](PF_6)_2$, which is an intermediate material, was synthesized. To be specific, $[PtCl_2(bpym)]$(41 mg, 0.10 mmol) and 3-$^t$BupzH (40 mg, 0.32 mmol) were stirred in water (5 mL) with heating at 80° C. for 4 hr. At this time, an orange suspension changed to a yellow solution. When $NH_4PF_6$ (73 mg, 0.45 mmol) was added to this yellow solution, precipitate was deposited. The yellow precipitate was collected by filtration, washed with water, and dried under reduced pressure. The yield was 54 mg, 63%. This reaction can be shown by the following chemical reaction formula.

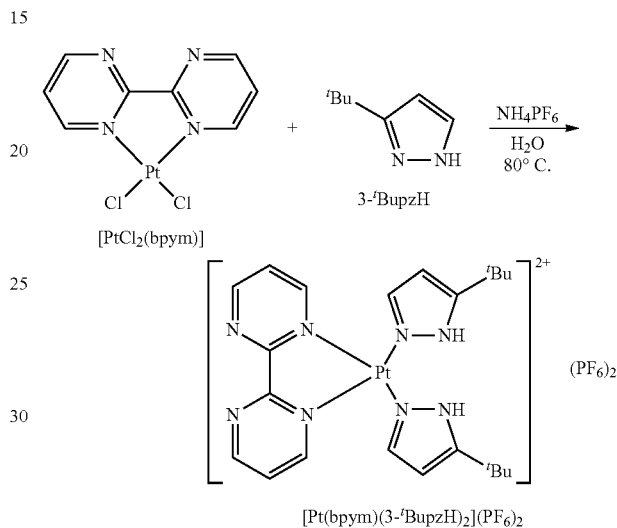

The obtained metal complex was readily soluble in acetonitrile, acetone, THF, DMF and DMSO, soluble in dichloromethane, methanol and ethanol, and hardly soluble in chloroform, hexane, toluene, benzene and diethylether.

Furthermore, the product was identified by IR and $^1$H NMR spectra.

The results of identification by IR spectrum are as follows.

IR(KBr): 3638 (w), 3364 (w), 3096 (w), 2968 (m), 1588 (s), 1558 (m), 1490 (m), 1412 (s), 1372 (w), 1303 (w), 1265 (w), 1211 (w), 1133 (m), 1070 (w), 1035 (w), 846 (s), 745 (m), 678 (w), 558 (s)

The results of identification by $^1$H NMR spectrum are as shown in the following Table 1. Each item in Table 1 denotes, from the left: δ for chemical shift of peak (ppm), Shape for the shape of peak, J for coupling constant (Hz), Int. for peak intensity (relative value), and Assign. for assignment of the peak.

TABLE 1

$^1$H NMR of $[Pt(bpym)(3\text{-}^tBupzH)_2](PF_6)_2$
(in CD$_3$CN, TMS, 300 MHz)

| δ(ppm) | shape (J/Hz) | Int. | Assign. |
|---|---|---|---|
| 11.91 | s, br | 2 | NH of $^t$BupzH |
| 9.40 | dd (1.9, 4.8) | 2 | H6 of bpym |
| 8.17 | dd (1.9, 5.9) | 2 | H4 of bpym |
| 7.87 | dd (4.8, 5.9) | 2 | H5 of bpym |
| 7.81 | d (2.4) | 2 | H5 of 3-$^t$BupzH |
| 6.47 | d (2.4) | 2 | H4 of 3-$^t$BupzH |
| 1.31 | s | 18 | $^t$Bu of 3-$^t$BupzH |

Furthermore, mass spectrometry was performed by the FAB-MS method. The results are as follows.

FAB-MS: m/z=746.6 [M-PF$_6$]$^+$

Then, using a mononuclear complex [Pt(bpym)(3-$^t$BupzH)$_2$](PF$_6$)$_2$, which is an intermediate material, a metal complex [Pt$_2$(bpym)$_2$(3-$^t$Bupz)$_2$(3-$^t$BupzH)$_2$](PF$_6$)$_2$ was synthesized. To be specific, KOH (12 mg, 0.21 mmol) was added to a solution (10 mL) of [Pt(bpym)(3-$^t$BupzH)$_2$](PF$_6$)$_2$ (86 mg, 0.10 mmol) in methanol, and the mixture was stirred at room temperature for 3 hr. The reaction solution changed from yellow to orange. This solution was concentrated to dryness under reduced pressure. Acetonitrile was added to the solid, and unreacted KOH was filtered off. The orange filtrate was dried to solidness and the solid was dissolved in dichloromethane. Hexane was added to this solution, and the precipitated orange solid was collected, washed with hexane, and dried under reduced pressure. The yield was 62 mg, 85%. This reaction can be shown by the following chemical reaction formula.

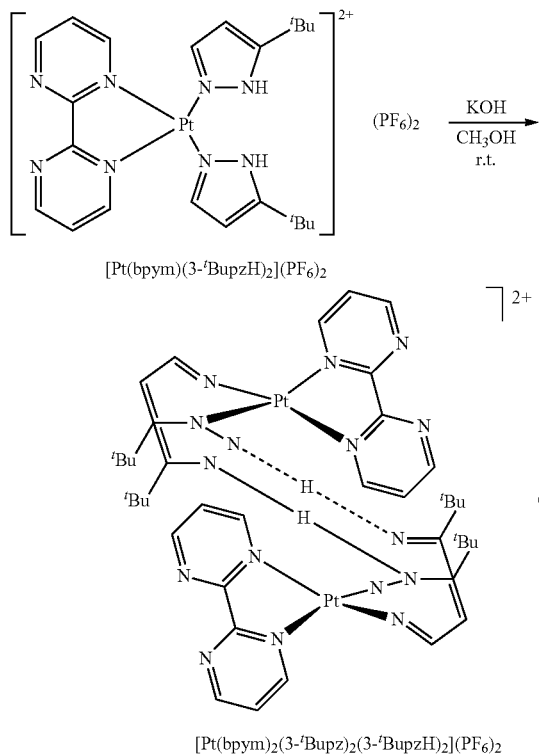

This metal complex exhibited orange emission under irradiation of UV light (365 nm). This metal complex was readily soluble in acetonitrile, dichloromethane, acetone, methanol, ethanol, benzene, DMF and DMSO, soluble in chloroform and toluene, and hardly soluble in water and hexane.

Furthermore, the product was identified by IR and $^1$H NMR spectra.

The results of identification by IR spectrum are as follows.
IR(KBr): 3082 (s), 2957 (s), 2864 (m), 1636 (w), 1584 (s), 1550 (m), 1493 (s), 1474 (m), 1459 (m), 1415 (s), 1362 (m), 1336 (m), 1236 (s), 1208 (m), 1121 (w), 1049 (s), 991 (w), 836 (s), 760 (m), 746 (s), 726 (w), 673 (m), 559 (s), 491 (w)

The results of identification by $^1$H NMR spectrum are as shown in the following Table 2. Each item in Table 2 is as defined in Table 1.

TABLE 2

$^1$H NMR data of [Pt$_2$(bpym)$_2$(3-$^t$Bupz)$_2$(3-$^t$BupzH)$_2$](PF$_6$)$_2$ (in CD$_3$CN, TMS, 300 MHz)

| δ(ppm) | shape (J/Hz) | Int. | Assign. |
|---|---|---|---|
| 9.29 | dd (2.0, 4.9) | 1 | H6 of bpym |
| 8.85 | dd (2.0, 5.8) | 1 | H4 of bpym |
| 7.80 | dd (4.9, 5.8) | 1 | H5 of bpym |
| 7.25 | d (2.1) | 1 | H5 of 3-$^t$Bupz |
| 6.21 | d (2.1) | 1 | H4 of 3-$^t$Bupz |
| 1.34 | s | 9 | $^t$Bu of 3-$^t$Bupz |

Furthermore, mass spectrometry was performed by the FAB-MS method. The results are as follows.

FAB-MS: m/z=1345.3 [M-PF$_6$]$^+$

Figure 2:
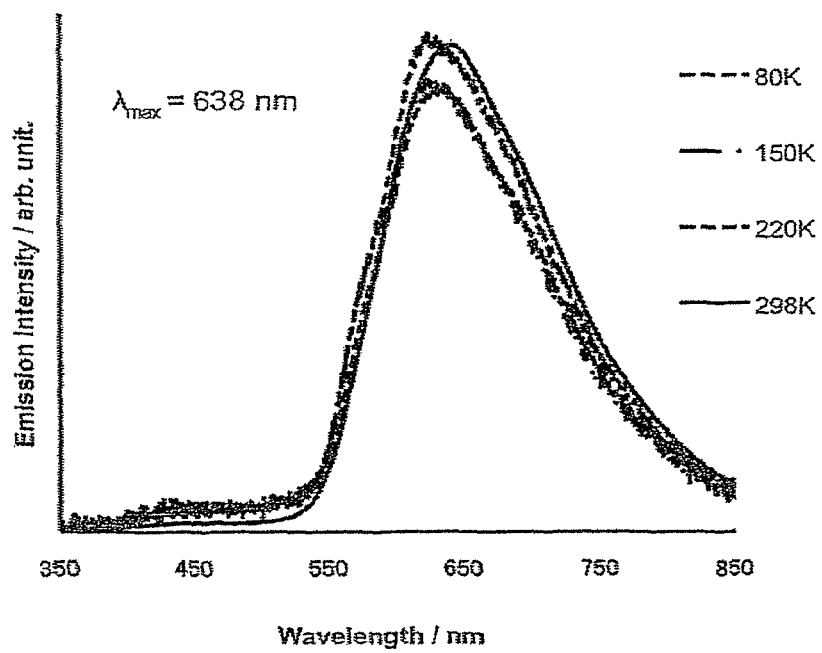
FIG. 2 shows emission spectra of [Pt$_2$(bpym)$_2$(3-$^t$Bupz)$_2$(3-$^t$BupzH)$_2$](PF$_6$)$_2$ in a solid state (measurement temperature: 80K, 150K, 220K, 298K).

The emission properties of the metal complex [Pt$_2$(bpym)$_2$(3-$^t$Bupz)$_2$(3-$^t$BupzH)$_2$](PF$_6$)$_2$ are now explained. The emission spectra of the metal complex in a solid state were measured. The emission spectra are shown in FIG. 2.

When [Pt$_2$(bpym)$_2$(3-$^t$Bupz)$_2$(3-$^t$BupzH)$_2$](PF$_6$)$_2$ in a solid state was excited with 355 nm UV light, a broad spectrum having an emission maximum at 638 nm was exhibited. In addition, the emission spectra measured at 298K, 220K, 150K and 80K did not show a remarkable change in the shape of the spectrum. The emission quantum yield (Φ) of the metal complex in a solid state was less than 0.01 and could not be measured.

Moreover, the emission decay curve of this metal complex in a solid state was measured, and analyzed using a biexponential function (I(t)=A$_1$exp(-t/τ$_1$)+A$_2$exp(-t/τ$_2$)) to give the values of τ$_1$, A$_1$, τ$_2$ and A$_2$. These results are described in the following Table 3. The emission lifetime of this metal complex is comparatively long and the emission is considered to occur from a triplet excited state (i.e., phosphorescence).

TABLE 3

|  | τ$_1$/μs | A$_1$ | τ$_2$/μs | A$_2$ |
|---|---|---|---|---|
| 80K | 0.05 | 0.76 | 0.32 | 0.24 |
| 150K | 0.04 | 0.82 | 0.24 | 0.18 |
| 220K | 0.04 | 0.80 | 0.21 | 0.20 |
| 298K | 0.03 | 0.89 | 0.10 | 0.11 |

Example 2

[Pt$_2$Ag$_2$(bpym)$_2$(3-$^t$Bupz)$_4$](PF$_6$)$_2$, which is one kind of the metal complex of the present invention, was synthesized. This metal complex has a constitution wherein, in the above-mentioned formula (C1), M$^{II}$ is Pt$^{II}$, M$^I$ is Ag$^I$, L$_C$ is bpym, L$_B$ is 3-$^t$Bupz, and the counter anion is PF$_6^-$.

First, a mononuclear complex [Pt(bpym)(3-$^t$BupzH)$_2$](PF$_6$)$_2$ was synthesized as an intermediate material in the same manner as in the method explained in Example 1.

Then, using the mononuclear complex [Pt(bpym)(3-$^t$BupzH)$_2$](PF$_6$)$_2$ which is an intermediate material, [Pt$_2$Ag$_2$(bpym)$_2$(3-$^t$Bupz)$_4$](PF$_6$)$_2$ was synthesized. To be specific, AgBF$_4$ (17 mg, 0.089 mmol) and triethylamine (49 μL, 0.31 mmol) were added to a solution (10 mL) of [Pt(bpym)(3-$^t$BupzH)$_2$](PF$_6$)$_2$ (69 mg, 0.078 mmol) in methanol, and the mixture was stirred under shading at room temperature for 3 hr. At this time, the yellow solution changed to a yellow suspension. The yellow solid was collected, washed with water and methanol, and dried under reduced pressure. The yield was 50 mg, 76%. This reaction can be shown by the following chemical reaction formula.

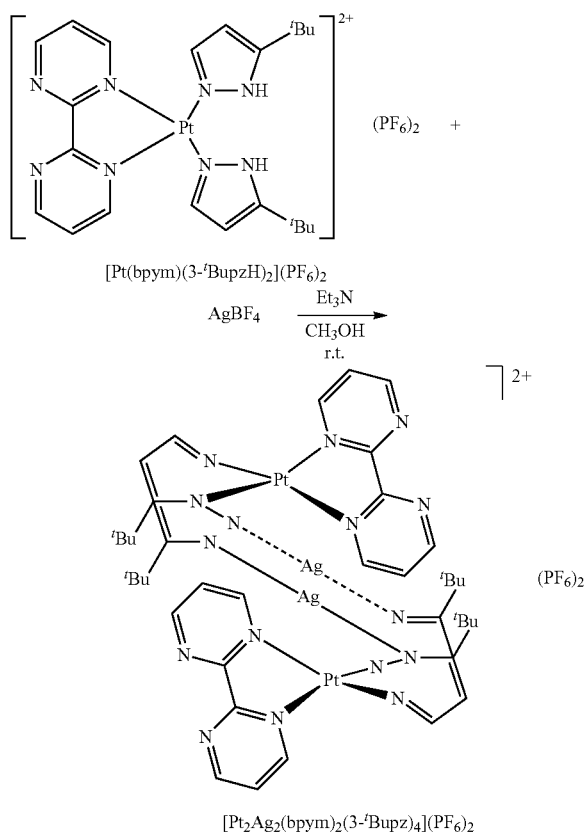

[Pt(bpym)(3-^tBupzH)_2](PF_6)_2

[Pt_2Ag_2(bpym)_2(3-^tBupz)_4](PF_6)_2

Furthermore, recrystallization from acetonitrile/ethanol was performed to give a single crystal. The obtained metal complex was a yellow solid. This metal complex exhibited green emission under irradiation of UV light (365 nm). This metal complex was readily soluble in acetonitrile, DMF and DMSO, soluble in dichloromethane, chloroform, acetone, methanol, THF and toluene, and hardly soluble in diethyl ether, ethanol, hexane, benzene and water.

Furthermore, the product was identified by IR and $^1$H NMR spectra, and elemental analysis.

The results of identification by IR spectrum are as follows.
IR(KBr): 3108 (w), 2954 (m), 2922 (m), 2860 (w), 1584 (s), 1552 (m), 1495 (m), 1458 (w), 1409 (s), 1360 (w), 1333 (m), 1247 (m), 1207 (w), 1178 (w), 1143 (w), 1081 (m), 1033 (w), 845 (s), 810 (m), 778 (w), 761 (m), 748 (s), 697 (w), 675 (w), 652 (w), 558 (s), 502 (w)

The results of identification by $^1$H NMR spectrum are as shown in the following Table 4. Each item in Table 4 is as defined in Table 1.

TABLE 4

$^1$H NMR data of [Pt_2Ag_2(bpym)_2(3-^tBupz)_4](PF_6)_2
(in CD_3CN; TMS, 400 MHz, −50° C.)

| δ(ppm) | shape (J/Hz) | Int. | Assign. |
|---|---|---|---|
| 9.37 | dd (2.0, 4.8) | 1 | H6 of bpym |
| 8.15 | dd (2.0, 5.7) | 1 | H4 of bpym |
| 7.91 | dd (4.8, 5.7) | 1 | H5 of bpym |
| 7.57 | d (2.2) | 1 | H5 of 3-^tBupz |
| 6.20 | d (2.2) | 1 | H4 of 3-^tBupz |
| 0.90 | s | 9 | ^tBu of 3-^tBupz |

The results of the elemental analysis of the product are shown in Table 5 in comparison with the calculated values. Here, each item in Table 5 denotes, from the left: calcd for calculated value, found for analyzed value, and Δ for difference between them (analyzed value-calculated value).

TABLE 5

Elemental analysis of [Pt_2Ag_2(bpym)_2(3-^tBupz)_4](PF_6)_2

|  | calcd | found | Δ |
|---|---|---|---|
| H (%) | 3.31 | 3.17 | −0.14 |
| C (%) | 31.00 | 31.13 | 0.13 |
| N (%) | 13.15 | 13.23 | 0.08 |

The structure of the obtained metal complex is explained. The molecular structure of the obtained metal complex was determined by single crystal X-ray structural analysis. The crystallographic data thereof are shown in Table 6. Here, the items in Table 6 denote, from the top: composition, formula weight, measurement temperature, measurement wavelength (MoKα ray=0.71070 Å), crystal system, space group, lattice constants (a, b, c, β), cell volume, Z value, density, linear absorption coefficient, number of unique reflections, final R index, R_1 index, and GOF value.

TABLE 6

Crystallographic data for [Pt_2Ag_2(bpym)_2(3-^tBupz)_4](PF_6)_2

| Empirical Formula | C_44H_56Ag_2F_12N_16P_2Pt_2 |
|---|---|
| Fw | 1704.85 |
| T, K | 296 |
| λ, Å | 0.71070 |
| Cryst Syst | monoclinic |
| Space Group | P2_1/c (# 14) |
| a, Å | 11.2312(4) |
| b, Å | 22.3248(7) |
| c, Å | 11.4090(4) |
| β, deg | 100.9752(4) |
| V, Å$^3$ | 2808.3(2) |
| Z | 2 |
| ρ_{calcd}, g cm$^{-3}$ | 2.016 |
| μ(Mo Kα), cm$^{-1}$ | 57.76 |
| No. of Reflections Measured | Unique: 6275 (R_{int} = 0.024) |
| Residuals: R; Rw | 0.049; 0.091 |
| Residuals: R1 | 0.033 |
| GOF | 1.04 |

Figure 3:
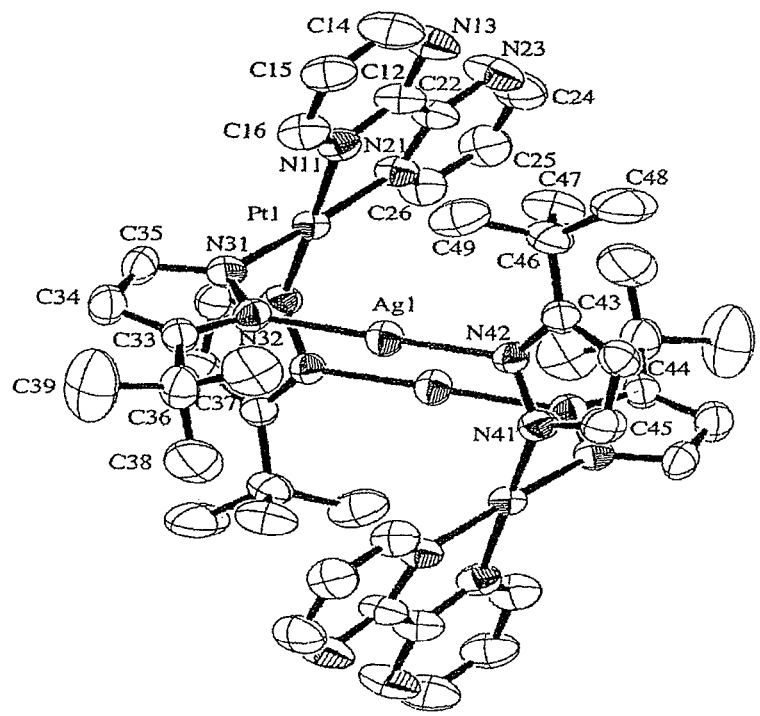
FIG. 3 is an ORTEP diagram showing the structure of a cation in [Pt$_2$Ag$_2$(bpym)$_2$(3-$^t$Bupz)$_4$](PF$_6$)$_2$.

In addition, the structure of cation in this metal complex is shown in the ORTEP diagram of FIG. 3. As shown in FIG. 3, two Pt atoms and two Ag atoms are contained in this cation. A crystallographically imposed center of symmetry is located at the midpoint between Ag . . . Ag, and half of the atoms in the crystals are independent. Bipyrimidine (bpym) coordinates as a bidentate chelating ligand to each Pt atom, and two 3-t-butylpyrazolato ligands (3-^tBupz) also coordinate with N atom located farther from t-butyl group to the residual coordination site. Each Pt atom forms a {(bpym)Pt(3-t-Bupz)_2} unit, and two 3-t-Bupz ligands of each unit coordinate to different Ag atoms, whereby a 12-membered ring containing two Pt atoms and two Ag atoms is formed. In [Pt_2Ag_2(bpym)_2(3-^tBupz)_4](PF_6)_2, the Pt . . . Ag distances are 3.4825(4) Å and 3.6142(4) Å, and the Ag . . . Ag distance is 3.0358(8)A. The Pt—N distances are within the range of 1.976(4) Å-2.032(4) Å, and the Ag—N distances are 2.105(4) Å and 2.112(4) Å.

Figure 4:
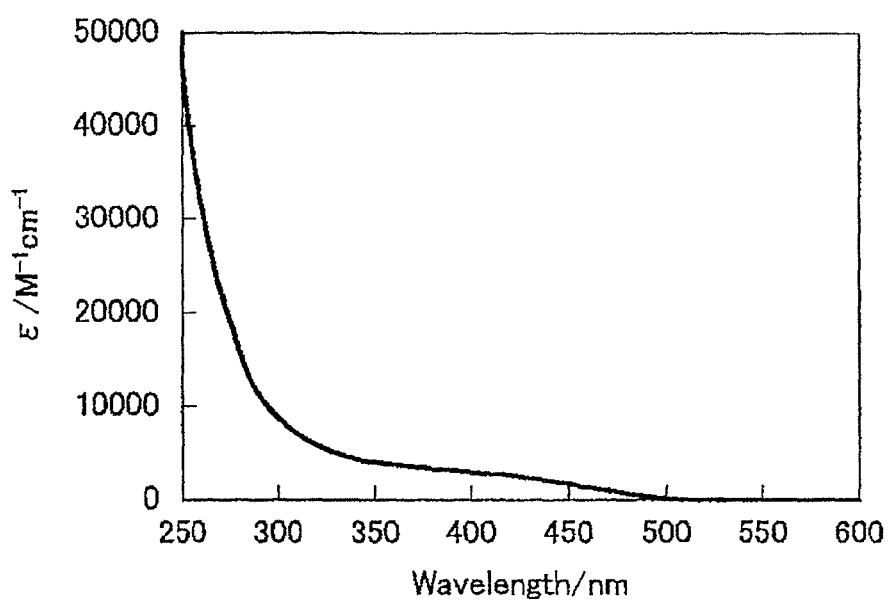
FIG. 4 shows an UV-vis absorption spectrum of a solution of [Pt$_2$Ag$_2$(bpym)$_2$(3-$^t$Bupz)$_4$](PF$_6$)$_2$ in acetonitrile.
Figure 5:
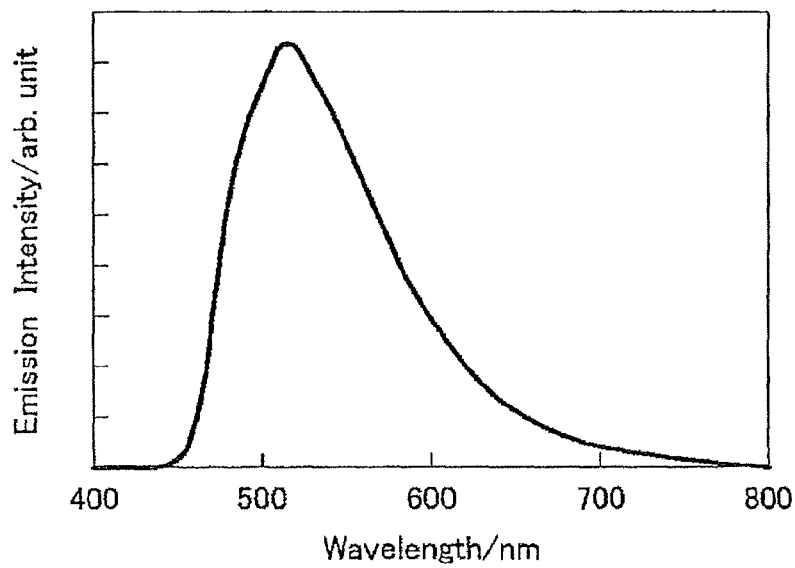
FIG. 5 shows an emission spectrum of [Pt$_2$Ag$_2$(bpym)$_2$(3-$^t$Bupz)$_4$](PF$_6$)$_2$ in a solid state (measurement temperature: 298K).

The emission properties of the metal complex [Pt_2Ag_2(bpym)_2(3-^tBupz)_4](PF_6)_2 are now explained. The UV-vis absorption spectrum of the acetonitrile solution of the metal complex and emission spectrum thereof in a solid state were measured. The ultraviolet-visible absorption spectrum of this acetonitrile solution is shown in FIG. 4, and the emission spectrum in the solid state is shown in FIG. 5.

The acetonitrile solution of [Pt$_2$Ag$_2$(bpym)$_2$(3-$^t$Bupz)$_4$](PF$_6$)$_2$ shows an absorption band based on the π-π* transition of the bipyrimidine ligand on the short wavelength side from 250 nm, and a broad absorption band at around 350-500 nm. In addition, when the metal complex in a solid state was excited with 355 nm UV light at 298K, a spectrum having an emission maximum at 516 nm was obtained. In [Pt$_2$Ag$_2$(bpym)$_2$(3-$^t$Bupz)$_4$](PF$_6$)$_2$, a vibrational structure of the emission spectrum is not clear. The emission quantum yield (Φ) of the metal complex in a solid state was 0.181.

Moreover, the emission decay curve of this metal complex in a solid state was measured, and analyzed using a monoexponential function to give the value of τ=1.10 μs (measurement temperature: 298K). The emission lifetime of this metal complex is comparatively long and the emission is considered to occur from a triplet excited state (i.e., phosphorescence).

Example 3

[Pt$_2$Au$_2$(bpym)$_2$(3-$^t$Bupz)$_4$](PF$_6$)$_2$, which is one kind of the metal complex of the present invention, was synthesized. This metal complex has a constitution wherein, in the above-mentioned formula (C1), M$^{II}$ is Pt$^{II}$, M$^I$ is Au$^I$, L$_C$ is bpym, L$_B$ is 3-$^t$Bupz, and the counter anion is PF$_6^-$.

First, a mononuclear complex [Pt(bpym)(3-$^t$BupzH)$_2$](PF$_6$)$_2$ was synthesized as an intermediate material in the same manner as in the method explained in Example 1.

Then, using the mononuclear complex [Pt(bpym)(3-$^t$BupzH)$_2$](PF$_6$)$_2$ which is an intermediate material, [Pt$_2$Au$_2$(bpym)$_2$(3-$^t$Bupz)$_4$](PF$_6$)$_2$ was synthesized. To be specific, AuCl(SC$_4$H$_8$) (56 mg, 0.17 mmol) and triethylamine (54 μL, 0.34 mmol) were added to a solution (10 mL) of [Pt(bpym) (3-$^t$BupzH)$_2$](PF$_6$)$_2$ (153 mg, 0.17 mmol) in methanol, and the mixture was stirred under an argon atmosphere at room temperature for 1 hr. At this time, the yellow solution changed to a yellow suspension. A yellow solid was collected, washed with water and methanol, and dried under reduced pressure.

The yield was 114 mg, 71%. This reaction can be shown by the following chemical reaction formula.

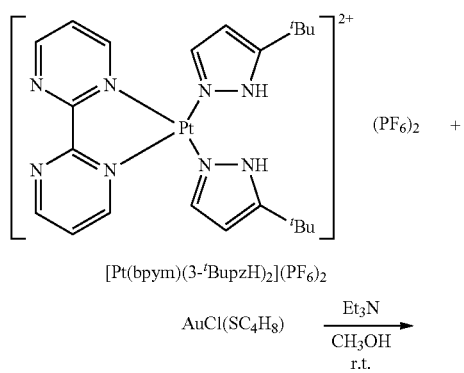

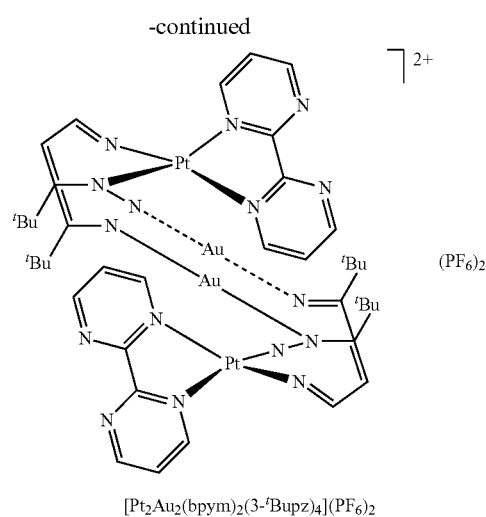

[Pt$_2$Au$_2$(bpym)$_2$(3-$^t$Bupz)$_4$](PF$_6$)$_2$

Furthermore, recrystallization from acetonitrile/ethanol was performed to give a single crystal. The obtained metal complex was a yellow solid. This metal complex exhibited dark green emission under irradiation of UV light (365 nm). This metal complex was readily soluble in acetonitrile, acetone, DMF and DMSO, and hardly soluble in chloroform, dichloromethane, methanol, diethyl ether, ethanol, THF, toluene, benzene and hexane.

Furthermore, the product was identified by IR and $^1$H NMR spectra.

The results of identification by IR spectrum are as follows.

IR(KBr): 3120 (w), 2953 (m), 2866 (w), 1585 (s), 1552 (m), 1486 (m), 1458 (w), 1409 (s), 1359 (w), 1333 (m), 1251 (m), 1209 (w), 1182 (w), 1149 (w), 1101 (w), 1034 (w), 1017 (w), 962 (w), 844 (s), 810 (m), 782 (w), 766 (m), 748 (m), 717 (w), 698 (w), 676 (w), 654 (w), 558 (s), 515 (w), 761 (m), 748 (s), 697 (w), 675 (w), 652 (w), 558 (s), 502 (w)

The results of identification by $^1$H NMR spectrum are as shown in the following Table 7. Each item in Table 7 is as defined in Table 1.

TABLE 7

$^1$H NMR data of [Pt$_2$Au$_2$(bpym)$_2$(3-$^t$Bupz)$_4$](PF$_6$)$_2$
(in CD$_3$CN, TMS, 300 MHz)

| δ(ppm) | shape (J/Hz) | Int. | Assign. |
|---|---|---|---|
| 9.43 | dd (2.0, 4.9) | 1 | H6 of bpym |
| 8.48 | dd (2.0, 5.8) | 1 | H4 of bpym |
| 7.95 | dd (4.9, 5.8) | 1 | H5 of bpym |
| 7.57 | d (2.4) | 1 | H5 of 3-$^t$Bupz |
| 6.22 | d (2.4) | 1 | H4 of 3-$^t$Bupz |
| 1.02 | s | 9 | $^t$Bu of 3-$^t$Bupz |

Furthermore, mass spectrometry was performed by the FAB-MS method. The results are as follows.

FAB-MS: m/z=1737.3 [M-PF$_6$]$^+$

The structure of the obtained metal complex is explained. The molecular structure of the obtained metal complex was determined by single crystal X-ray structural analysis. The crystallographic data are shown in Table 8. Here, each item in Table 8 is as defined in Table 6.

TABLE 8

Crystallographic data for [Pt$_2$Au$_2$(bpym)$_2$(3-$^t$Bupz)$_4$](PF$_6$)$_2$

| | |
|---|---|
| Empirical Formula | C$_{44}$H$_{56}$Au$_2$F$_{12}$N$_{16}$P$_2$Pt$_2$ |
| Fw | 1883.06 |
| T, K | 296 |
| λ, Å | 0.71070 |
| Cryst Syst | monoclinic |
| Space Group | P2$_1$/c (# 14) |
| a, Å | 11.2563(4) |
| b, Å | 22.4540(8) |
| c, Å | 11.3055(4) |
| β, deg | 100.4349(5) |
| V, Å$^3$ | 2810.2(2) |
| Z | 2 |
| ρ$_{calcd}$, g cm$^{-3}$ | 2.225 |
| μ(Mo Kα), cm$^{-1}$ | 103.10 |
| No. of Reflections Measured | Unique: 6399 (R$_{int}$ = 0.026) |
| Residuals: R; Rw | 0.041; 0.066 |
| Residuals: R1 | 0.027 |
| GOF | 0.96 |

Figure 6:
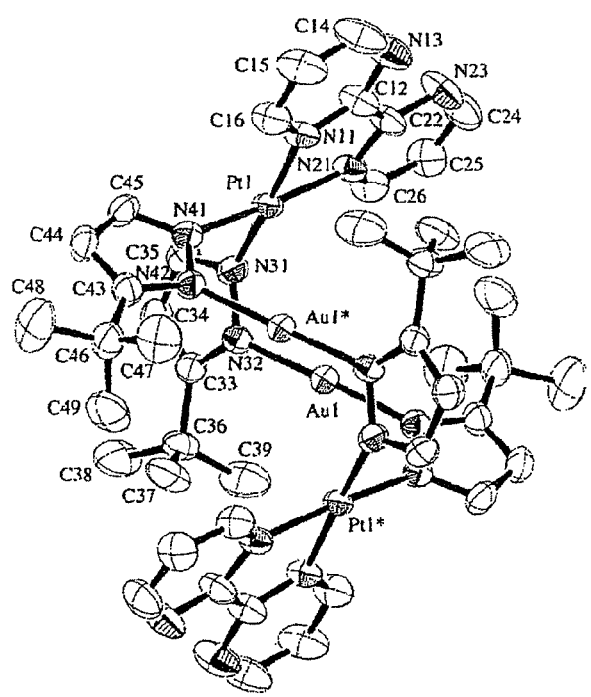
FIG. 6 is an ORTEP diagram showing the structure of a cation in [Pt$_2$Au$_2$(bpym)$_2$(3-$^t$Bupz)$_4$](PF$_6$)$_2$.

In addition, the structure of cation in this metal complex is shown in the ORTEP diagram of FIG. 6. As shown in FIG. 6, two Pt atoms and two Au atoms are contained in this cation. A crystallographically imposed center of symmetry is located at the midpoint between Au . . . Au, and half of the atoms in the crystals are independent. Bipyrimidine (bpym) coordinates as a bidentate chelating ligand to each Pt atom, and two 3-t-butylpyrazolato ligands (3-$^t$Bupz) also coordinate with N atom located farther from t-butyl group to the residual coordination site. Each Pt atom forms a {(bpym)Pt(3-t-Bupz)$_2$} unit, and two 3-t-Bupz ligands of each unit coordinate to different Ag atoms, whereby a 12-membered ring containing two Pt atoms and two Au atoms is formed. In [Pt$_2$Au$_2$(bpym)$_2$(3-$^t$Bupz)$_4$](PF$_6$)$_2$, the Pt . . . Au distances are 3.5148(3) Å and 3.5941(3) Å, and the Au . . . Au distance is 3.2377(4) Å. The Pt—N distances are within the range of 1.992(4) Å-2.019(4) Å, and the Au—N distance are 2.012(4) Å and 2.019(4) Å.

Figure 7:
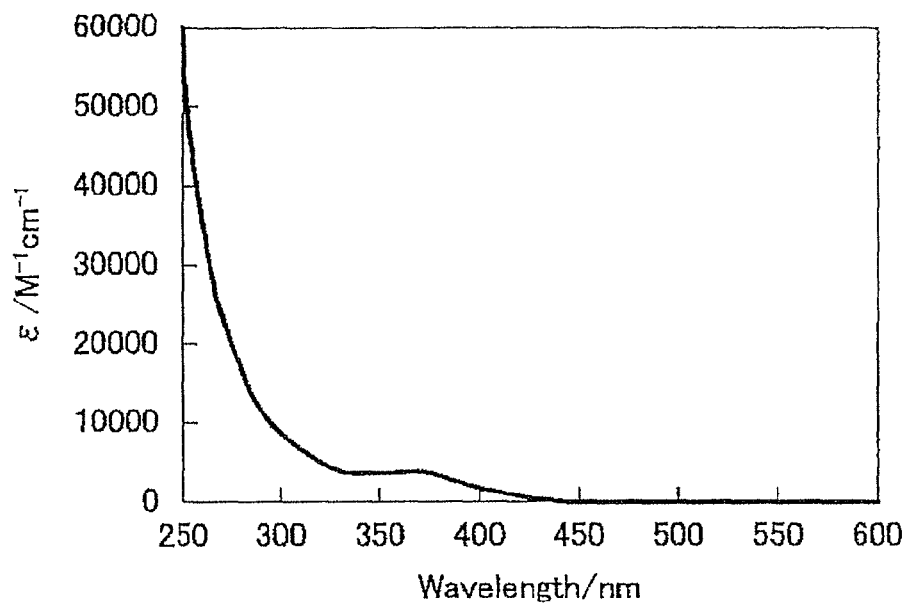
FIG. 7 shows an UV-vis absorption spectrum of a solution of [Pt$_2$Au$_2$(bpym)$_2$(3-$^t$Bupz)$_4$](PF$_6$)$_2$ in acetonitrile.
Figure 8:
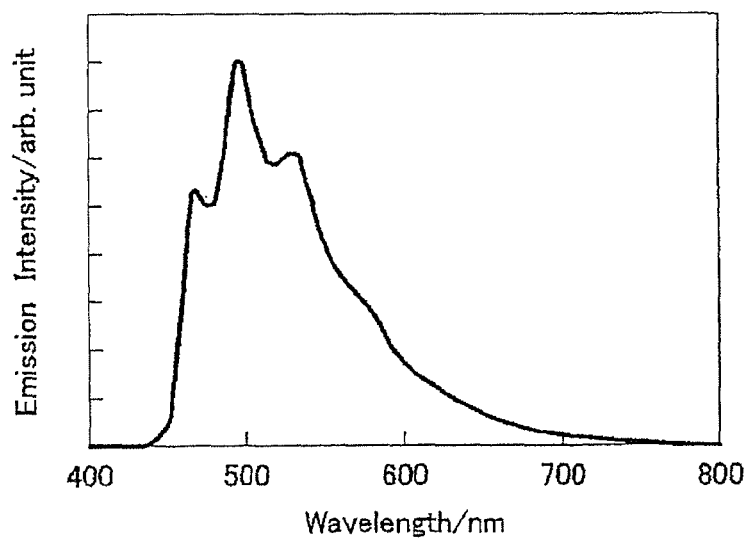
FIG. 8 shows an emission spectrum of [Pt$_2$Au$_2$(bpym)$_2$(3-$^t$Bupz)$_4$](PF$_6$)$_2$ in a solid state (measurement temperature: 298K).

The emission properties of the metal complex [Pt$_2$Au$_2$(bpym)$_2$(3-$^t$Bupz)$_4$](PF$_6$)$_2$ are now explained. The UV-vis absorption spectrum of the acetonitrile solution of the metal complex and emission spectrum thereof in a solid state were measured. The UV-vis absorption spectrum of this acetonitrile solution is shown in FIG. 7, and the emission spectrum in the solid state is shown in FIG. 8.

The acetonitrile solution of [Pt$_2$Au$_2$(bpym)$_2$(3-$^t$Bupz)$_4$](PF$_6$)$_2$ shows an absorption band based on the π-π* transition of the bipyrimidine ligand on the short wavelength side from 250 nm, and the absorption maximum at 365 nm. In addition, when the metal complex in a solid state was excited with 355 nm UV light at 298K, the spectrum with an emission maximum wavelength at 494 nm was obtained. The emission quantum yield (Φ) of the metal complex in a solid state was 0.074.

Moreover, the emission decay curve of this metal complex in a solid state was measured, and analyzed using a biexponential function (I(t)=A$_1$exp(-t/τ$_1$)+A$_2$exp(-t/τ$_2$)) to give the values of τ$_1$=0.39 μs, A$_1$=0.42, τ$_2$=1.32 μs and A$_2$=0.58 (measurement temperature: 298K). The emission lifetime of this metal complex is comparatively long and the light is considered to be emitted from a triplet excited state (i.e., phosphorescence).

Example 4

[Pt$_2$Cu$_2$(bpym)$_2$(3-$^t$Bupz)$_4$](PF$_6$)$_2$, which is one kind of the metal complex of the present invention, was synthesized. This metal complex has a constitution wherein, in the abovementioned formula (C1), M$^{II}$ is Pt$^{II}$, M$^{I}$ is Cu$^{I}$, L$_C$ is bpym, L$_B$ is 3-$^t$Bupz, and the counter anion is PF$_6^-$.

First, a mononuclear complex [Pt(bpym)(3-$^t$BupzH)$_2$](PF$_6$)$_2$ was synthesized as an intermediate material in the same manner as in the method explained in Example 1.

Then, using the mononuclear complex [Pt(bpym)(3-$^t$BupzH)$_2$](PF$_6$)$_2$, which is an intermediate material, [Pt$_2$Cu$_2$(bpym)$_2$(3-$^t$Bupz)$_4$](PF$_6$)$_2$ was synthesized. To be specific, [Cu(CH$_3$CN)$_4$](BF$_4$) (23 mg, 0.072 mmol) and triethylamine (44.5 μL, 0.28 mmol) were added with stirring to a solution (10 mL) of [Pt(bpym)(3-$^t$BupzH)$_2$](PF$_6$)$_2$ (63 mg, 0.071 mmol) in methanol, and the mixture was stirred under an argon atmosphere at room temperature for 2 hr. The yellow precipitate was collected, washed with water and methanol, and dried under reduced pressure. The yield was 41 mg, 71%. This reaction can be shown by the following chemical reaction formula.

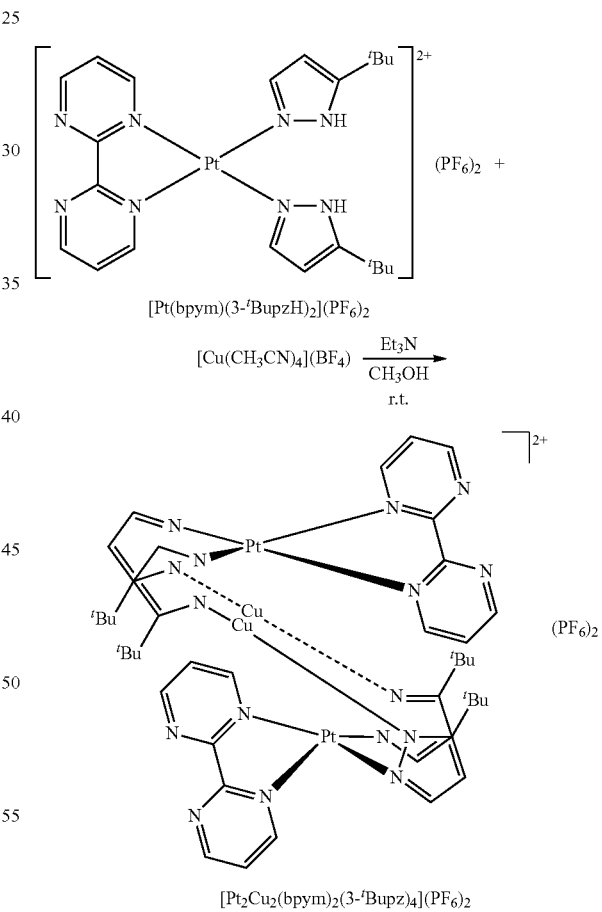

This metal complex was readily soluble in acetonitrile, acetone, benzene, DMF and DMSO, soluble in chloroform, dichloromethane, methanol, diethyl ether and THF, and hardly soluble in toluene, hexane, ethanol and water.

Furthermore, the product was identified by IR spectrum. The results of identification by IR spectrum are as shown below.

IR(KBr): 3107 (w), 2955 (m), 2876 (w), 1585 (s), 1552 (m), 1496 (m), 1459 (m), 1410 (s), 1362 (w), 1331 (m), 1248 (m), 1209 (w), 1180 (w), 1142 (w), 1082 (m), 1033 (w), 1017 (w), 845 (s), 810 (m), 777 (m), 765 (m), 748 (s), 722 (w), 697 (w), 676 (m), 652 (w), 558 (s), 504 (w)

Figure 9:
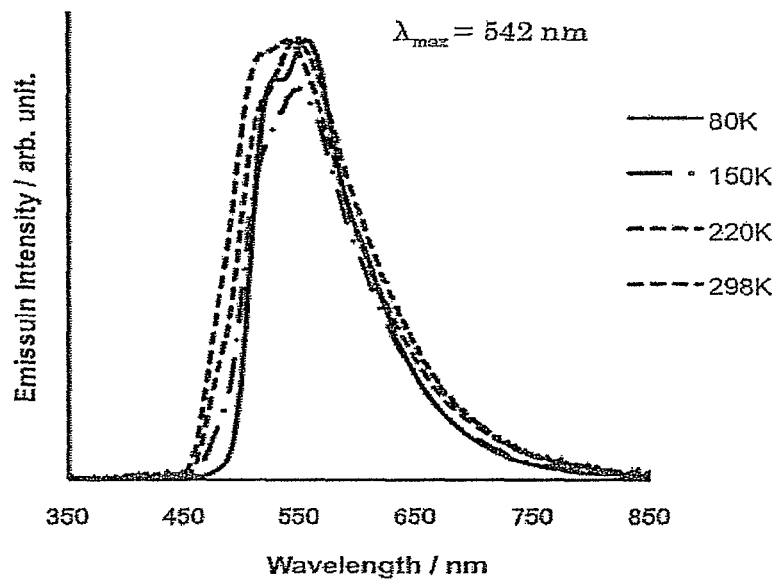
FIG. 9 shows emission spectra of [Pt$_2$Cu$_2$(bpym)$_2$(3-$^t$Bupz)$_4$](PF$_6$)$_2$ in a solid state (measurement temperature: 80K, 150K, 220K, 298K).

The emission properties of the metal complex $[Pt_2Cu_2(bpym)_2(3\text{-}^tBupz)_4](PF_6)_2$ are now explained. The emission spectra of the metal complex in a solid state were measured. The emission spectra are shown in FIG. 9.

When $[Pt_2Cu_2(bpym)_2(3\text{-}^tBupz)_4](PF_6)_2$ in a solid state was excited with 355 nm UV light at 298K, the broad spectrum with an emission maximum wavelength at around 542 nm was exhibited. As the measurement temperature lowered, a vibrational structure gradually appeared in the emission spectrum. The emission quantum yield (Φ) of the metal complex in a solid state was 0.008.

Moreover, the emission decay curve of this metal complex in a solid state was measured, and analyzed using a biexponential function ($I(t)=A_1\exp(-t/\tau_1)+A_2\exp(-t/\tau_2)$) to give the values of $\tau_1$, $A_1$, $\tau_2$ and $A_2$. These results are described in the following Table 9. The emission lifetime of this metal complex is comparatively long and the emission is considered to occur from a triplet excited state (i.e., phosphorescence).

TABLE 9

|  | $\tau_1/\mu s$ | $A_1$ | $\tau_2/\mu s$ | $A_2$ |
|---|---|---|---|---|
| 80K | 1.12 | 0.59 | 4.64 | 0.41 |
| 150K | 0.64 | 0.61 | 2.29 | 0.39 |
| 220K | 0.26 | 0.64 | 1.04 | 0.36 |
| 298K | 0.11 | 0.84 | 0.34 | 0.16 |

Example 5

$[Pt_2(bpy)_2(3\text{-}^tBupz)_2](3\text{-}^tBupzH)_2(PF_6)_2$, which is one kind of the metal complex of the present invention, was synthesized. This metal complex has a constitution wherein, in the above-mentioned formula (C1), $M^{II}$ is $Pt^{II}$, $M^I$ is $H^+$, $L_C$ is bpy, $L_B$ is 3-$^tBupz$, and the counter anion is $PF_6^-$. Two $H^+$ and two 3-$^tBupz$ are bonded to form two 3-$^tBupzH$. The bpy is 2,2'-bipyridine.

First, a mononuclear complex $[Pt(bpy)(3\text{-}^tBupzH)_2](PF_6)_2$, which is an intermediate material, was synthesized. To be specific, $[PtCl_2(bpy)]$ (42 mg, 0.10 mmol) and 3-$^tBupzH$ (40 mg, 0.32 mmol) were stirred in water (5 mL) with heating at 80° C. for 4 hr. At this time, the yellow suspension changed to a yellow solution. When $NH_4PF_6$ (74 mg, 0.45 mmol) was added to this yellow solution, white-yellow precipitate was deposited. This precipitate was collected by filtration, washed with water and dried under reduced pressure. The yield was 35 mg, 39%. This reaction can be shown by the following chemical reaction formula.

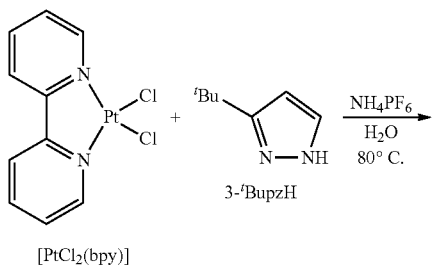

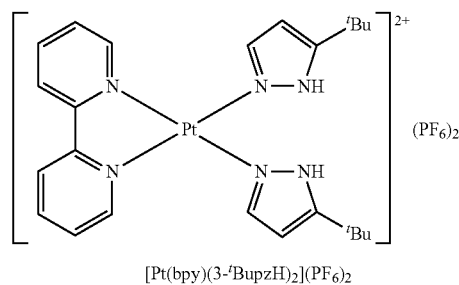

$[Pt(bpy)(3\text{-}^tBupzH)_2](PF_6)_2$

The obtained metal complex was readily soluble in acetonitrile, acetone and benzene, soluble in DMSO, and hardly soluble in diethyl ether, ethanol, methylene chloride, chloroform, hexane, methanol and water.

Furthermore, the product was identified by IR spectrum. The results of identification by IR spectrum are as follows.

IR(KBr): 3356 (m), 3057 (w), 2967 (m), 2839 (m), 2366 (m), 1612 (s), 1567 (s), 1454 (s), 1368 (s), 1297 (s), 1246 (s), 1213 (s), 1134 (s), 1075 (s), 996 (s), 848 (m), 558 (s)

Furthermore, mass spectrometry was performed by the FAB-MS method. The results are as follows.

FAB-MS: $m/z=744.3$ $[M\text{-}PF_6]^+$

Then, using a mononuclear complex $[Pt(bpy)(3\text{-}^tBupzH)_2](PF_6)_2r$ which is an intermediate material, a metal complex $[Pt_2(bpy)_2(3\text{-}^tBupz)_2(3\text{-}^tBupzH)_2](PF_6)_2$ was synthesized. To be specific, KOH (11.6 mg, 0.21 mmol) was added to a solution (10 mL) of $[Pt(bpy)(3\text{-}^tBupzH)_2](PF_6)_2$ (41 mg, 0.05 mmol) in methanol, and the mixture was stirred at room temperature for 3 hr. The reaction solution changed from pale yellow to orange. This solution was concentrated to dryness under reduced pressure. Acetonitrile was added to the solid, and unreacted KOH was filtered off. The orange filtrate was dried to solidness. The solid was dissolved in dichloromethane, and hexane was added to this solution. The precipitated orange solid was collected, washed with hexane and dried under reduced pressure. The yield was 14.1 mg, 20%. This reaction can be shown by the following chemical reaction formula.

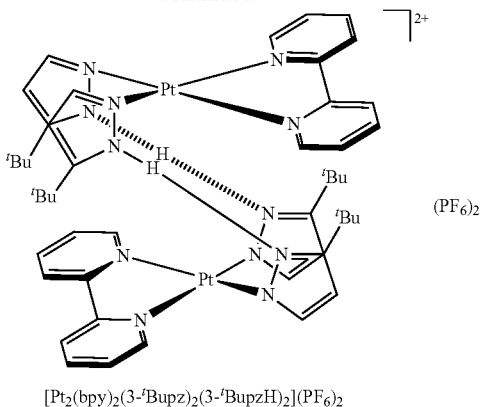

[Pt₂(bpy)₂(3-ᵗBupz)₂(3-ᵗBupzH)₂](PF₆)₂

This metal complex was readily soluble in chloroform, dichloromethane, acetonitrile, acetone, methanol, ethanol and DMF, soluble in benzene and hexane, and hardly soluble in water.

Furthermore, the product was identified by IR and ¹H NMR spectra.

The results of identification by IR spectrum are as follows.
IR(KBr): 2957 (s), 2361 (s), 1633 (m), 1451 (s), 1236 (m), 1047 (m), 834 (s), 762 (m), 559 (s), 279 (s)

The results of identification by ¹H NMR spectrum are as shown in the following Table 10. Each item in Table 10 is as defined in Table 1.

TABLE 10

¹H NMR data of [Pt₂(bpy)₂(3-ᵗBupz)₂(3-ᵗBupzH)₂](PF₆)₂
(in CD₃CN, TMS, 300 MHz)

| δ (ppm) | Shape(J/Hz) | Int. | Assign. |
|---|---|---|---|
| 8.71 | ddd (0.4, 1.6, 5.9) | 2 | H6 of bpy |
| 8.22 | ddd (0.8, 1.8, 8.3) | 2 | H3 of bpy |
| 8.18 | ddd (1.3, 6.2, 15.1) | 2 | H4 of bpy |
| 7.52 | ddd (1.7, 6.5, 13.2) | 2 | H5 of bpy |
| 7.01 | d (1.9) | 2 | H5 of 3-ᵗBupz |
| 5.95 | d (1.9) | 2 | H4 of 3-ᵗBupz |
| 1.31 | s | 18 | ᵗBu of 3-ᵗBupz |

Furthermore, mass spectrometry was performed by the FAB-MS method. The results are as follows.
FAB-MS: m/z=1341.6 [M-PF₆]⁺

Figure 10:
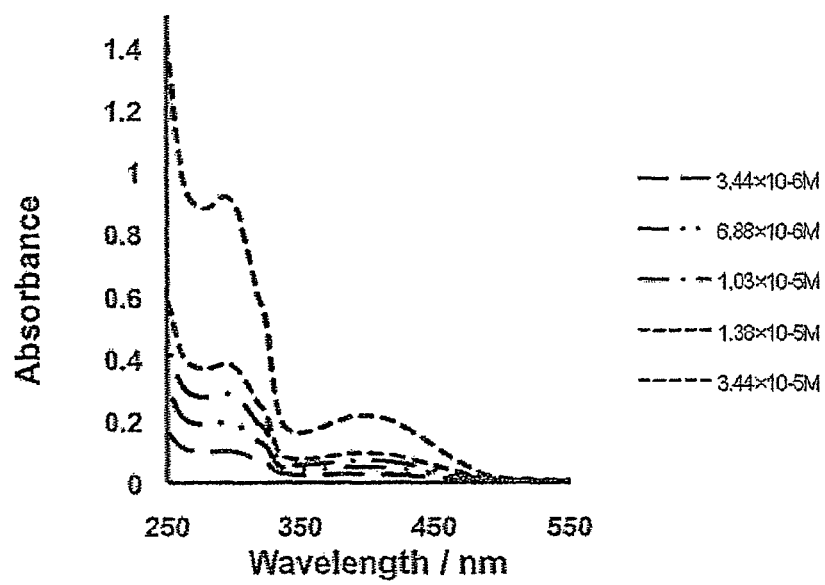
FIG. 10 shows UV-vis absorption spectra of solutions of [Pt$_2$(bpy)$_2$(3-$^t$Bupz)$_2$(3-$^t$BupzH)$_2$](PF$_6$)$_2$ in acetonitrile (concentration of metal complex: 3.44×10$^{-6}$M, 6.88×10$^{-6}$M, 1.03×10$^{-5}$M, 1.38×10$^{-5}$M, 3.44×10$^{-5}$M).
Figure 11:
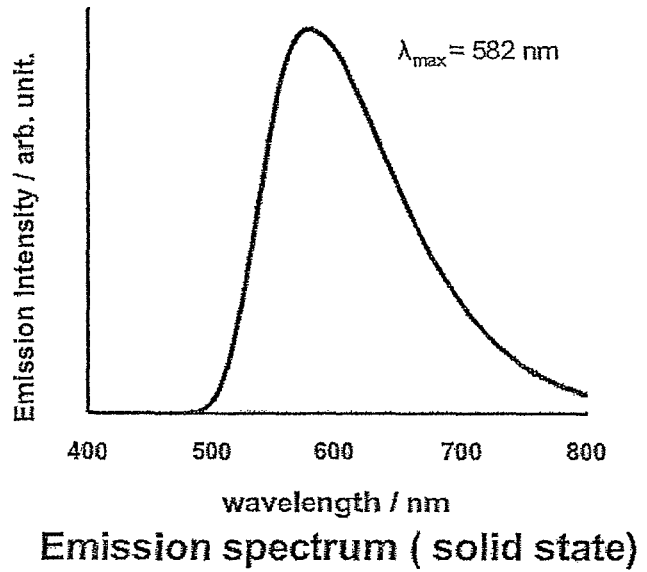
FIG. 11 shows an emission spectrum of [Pt$_2$(bpy)$_2$(3-$^t$Bupz)$_2$(3-$^t$BupzH)$_2$](PF$_6$)$_2$ in a solid state (measurement temperature: 298K).

The emission properties of the metal complex [Pt₂(bpy)₂(3-ᵗBupz)₂(3-ᵗBupzH)₂](PF₆)₂ are now explained. The UV-vis absorption spectra of the acetonitrile solutions of the metal complex and emission spectrum thereof in a solid state were measured. The UV-vis absorption spectra of the acetonitrile solutions are shown in FIG. 10, and the emission spectrum in the solid state is shown in FIG. 11.

A solution of [Pt₂(bpy)₂(3-ᵗBupz)₂](3-ᵗBupzH)₂(PF₆)₂ in acetonitrile having a concentration of $3.44 \times 10^{-5}$M shows a broad absorption band at around 350 nm-500 nm. In addition, when the metal complex in a solid state was excited with 355 nm UV light at 298K, a broad spectrum showing an emission maximum at 582 nm was obtained. The emission quantum yield (Φ) of the metal complex in a solid state was 0.11.

Moreover, the emission decay curve of this metal complex in a solid state was measured, and analyzed using a biexponential function $(I(t)=A_1\exp(-t/\tau_1)+A_2\exp(-t/\tau_2))$ to give the values of $\tau_1=0.10$ μs, $A_1=0.36$, $\tau_2=0.46$ μs and $A_2=0.64$ (measurement temperature: 298K). The emission lifetime of this metal complex is comparatively long and the emission is considered to occur from a triplet excited state (i.e., phosphorescence).

Example 6

[Pt₂Ag₂(bpy)₂(3-ᵗBupz)₄](PF₆)₂, which is one kind of the metal complex of the present invention, was synthesized. This metal complex has a constitution wherein, in the above-mentioned formula (C1), $M^{II}$ is $Pt^{II}$, $M^{I}$ is $Ag^{I}$, $L_C$ is bpy, $L_B$ is 3-ᵗBupz, and the counter anion is $PF_6^-$.

First, a mononuclear complex [Pt(bpy)(3-ᵗBupzH)₂](PF₆)₂ was synthesized as an intermediate material in the same manner as in the method explained in Example 5.

Then, using the mononuclear complex [Pt(bpy)(3-ᵗBupzH)₂](PF₆)₂, which is an intermediate material, a metal complex [Pt₂Ag₂(bpy)₂(3-ᵗBupz)₄](PF₆)₂ was synthesized. AgBF₄ (17 mg, 0.09 mmol) and triethylamine (50 μL, 0.31 mmol) were added to a solution (10 mL) of [Pt(bpy)(3-ᵗBupzH)₂](PF₆)₂ (70 mg, 0.08 mmol) in methanol, and the mixture was stirred under shading at room temperature for 3 hr. At this time, the yellow solution changed to a yellow-green suspension. The yellow-green solid was collected, washed with water and methanol, and dried under reduced pressure. The yield was 53 mg, 75%. This reaction can be shown by the following chemical reaction formula.

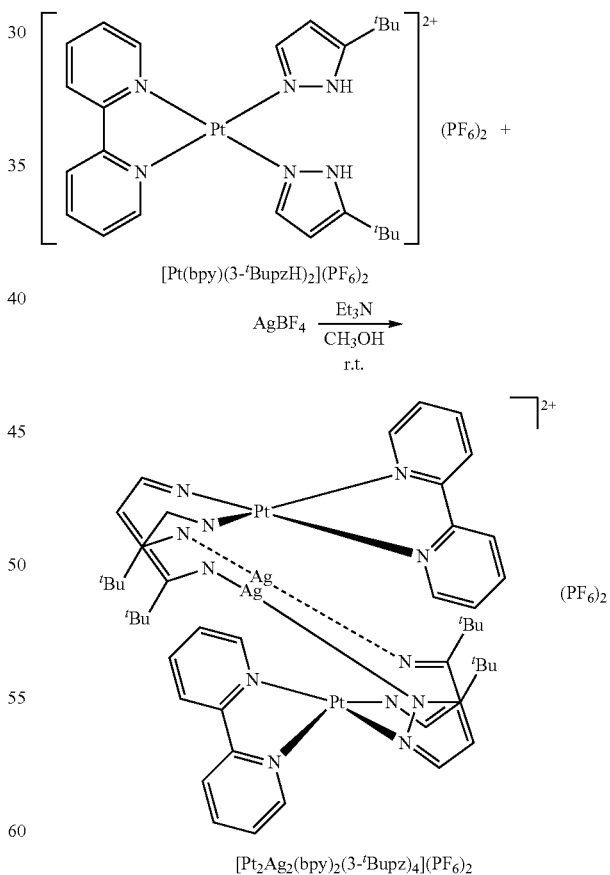

Furthermore, recrystallization from acetonitrile/methanol was performed to give a single crystal. The obtained metal complex was a yellow solid. This metal complex exhibited blue-green emission under irradiation of UV light (365 nm).

This metal complex was readily soluble in ethanol, dichloromethane, hexane, acetonitrile and acetone, soluble in diethyl ether, chloroform, DMSO and benzene, and hardly soluble in methanol and water.

Moreover, the product was identified by IR and $^1$H NMR spectra, and elemental analysis.

The results of identification by IR spectrum are as follows.

IR(KBr): 3439 (w), 3125 (m), 2950 (m), 2360 (m), 1610 (s), 1482 (m), 1455 (s), 1361 (m), 1328 (s), 1177 (s), 1136 (s), 1075 (m), 844 (m), 772 (s), 558 (s), 503 (m), 421 (m)

The results of identification by $^1$H NMR spectrum are as shown in the following Table 11. Each item in Table 11 is as defined in Table 1.

TABLE 11

$^1$H NMR data of $[Pt_2Ag_2(bpy)_2(3\text{-}^tBupz)_4](PF_6)_2$
(in $CD_3CN$, TMS, 400 MHz, −50° C.)

| δ (ppm) | Shape(J/Hz) | Int. | Assign. |
|---|---|---|---|
| 8.39 | dd (1.0, 5.4) | 2 | H6, H3 of bpy |
| 8.04 | d (5.6) | 1 | H4 of bpy |
| 7.76 | dd (5.4, 10.7) | 1 | H5 of bpy |
| 7.52 | dd (1.9, 2.7) | 1 | H5 of 3-$^t$Bupz |
| 6.10 | dd (2.0, 3.2) | 1 | H4 of 3-$^t$Bupz |
| 0.82 | s | 9 | $^t$Bu of 3-$^t$Bupz |

The results of elemental analysis of the product are shown in Table 12 in comparison with the calculated values. Here, each item in Table 12 is as defined in Table 5.

TABLE 12

|  | Calc. | Found. | Δ |
|---|---|---|---|
| C(%) | 33.89 | 33.97 | 0.08 |
| H(%) | 3.56 | 2.93 | −0.63 |
| N(%) | 9.88 | 9.89 | 0.01 |

Furthermore, mass spectrometry was performed by the FAB-MS method. The results are as follows.

FAB-MS: m/z=1555.3 $[M-PF_6]^+$

The structure of the obtained metal complex is explained. The molecular structure of the obtained metal complex was determined by single crystal X-ray structural analysis. The crystallographic data are shown in Table 13. Here, each item in Table 13 is as defined in Table 6.

TABLE 13

Crystallographic data for $[Pt_2Ag_2(bpym)_2(3\text{-}^tBupz)_4](PF_6)_2$

| Empirical Formula | $C_{48}H_{60}Ag_2F_{12}N_{12}P_2Pt_2$ |
|---|---|
| Fw | 1700.93 |
| T, K | 93 |
| λ, Å | 0.71075 |
| Cryst Syst | monoclinic |
| Space Group | $P2_1/c$ (# 14) |
| a, Å | 11.705(2) |
| b, Å | 11.5306(13) |
| c, Å | 21.179(3) |
| β, deg | 103.334(2) |
| V, Å$^3$ | 2781.5(6) |
| Z | 2 |
| $ρ_{calcd}$, g cm$^{-3}$ | 2.031 |
| μ(Mo Kα), cm$^{-1}$ | 58.296 |
| No. of Reflections Measured | Unique: 22342 ($R_{int}$ = 0.0364) |
| Residuals: R; Rw | 0.0265; 0.0456 |
| Residuals: R1 | 0.0222 |
| GOF | 1.002 |

Figure 12:
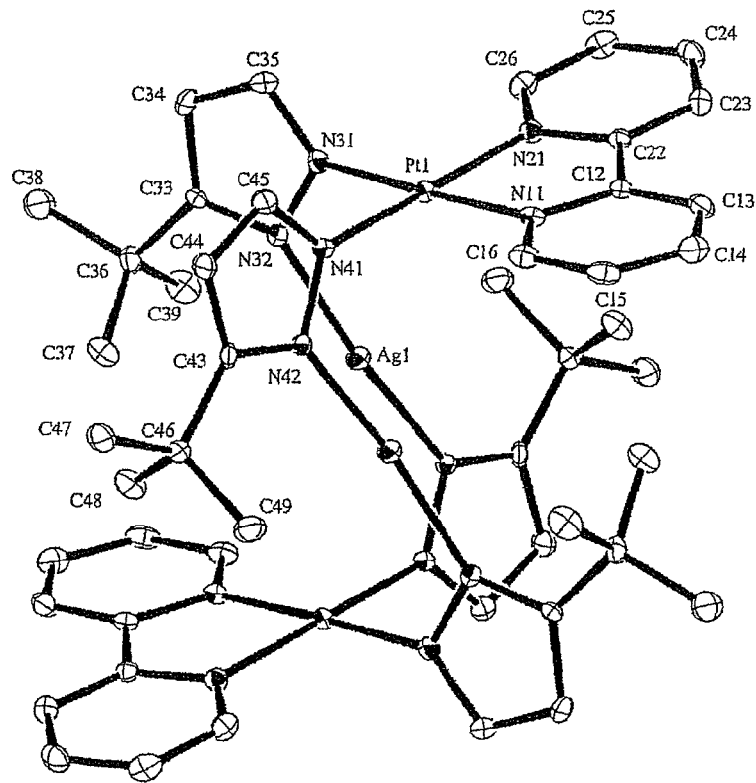
FIG. 12 is an ORTEP diagram showing the structure of a cation in [Pt$_2$Ag$_2$(bpy)$_2$(3-$^t$Bupz)$_4$](PF$_6$)$_2$.

In addition, the structure of cation in this metal complex is shown in the ORTEP diagram of FIG. 12. As shown in FIG. 12, two Pt atoms and two Ag atoms are contained in this cation. A crystallographically imposed center of symmetry is located at the midpoint between Ag . . . Ag, and half of the atoms in the crystals are independent. 2,2'-Bipyridine (bpy) coordinates as a bidentate chelating ligand to each Pt atom, and two 3-t-butylpyrazolato ligands (3-$^t$Bupz) coordinate with N atom located farther from t-butyl group to the residual coordination site. Each Pt atom forms a $\{(bpy)Pt(3\text{-}^tBupz)_2\}$ unit, and two 3-$^t$Bupz ligands of each unit coordinate to different Ag atoms, whereby a 12-membered ring containing two Pt atoms and two Ag atoms is formed. In $[Pt_2Ag_2(bpy)_2(3\text{-}^tBupz)_4](PF_6)_2$, the Pt . . . Pt distance is 5.8256(7) Å, the Pt . . . Ag distances are 3.4562(5) and 3.6502(4) Å, and the Ag . . . Ag distance is 3.0545(5) Å. The Pt—N distances are within the range of 1.989(3)-2.012(3) Å, and the Ag—N distances are 2.090(3) Å and 2.096(3) Å.

Figure 13:
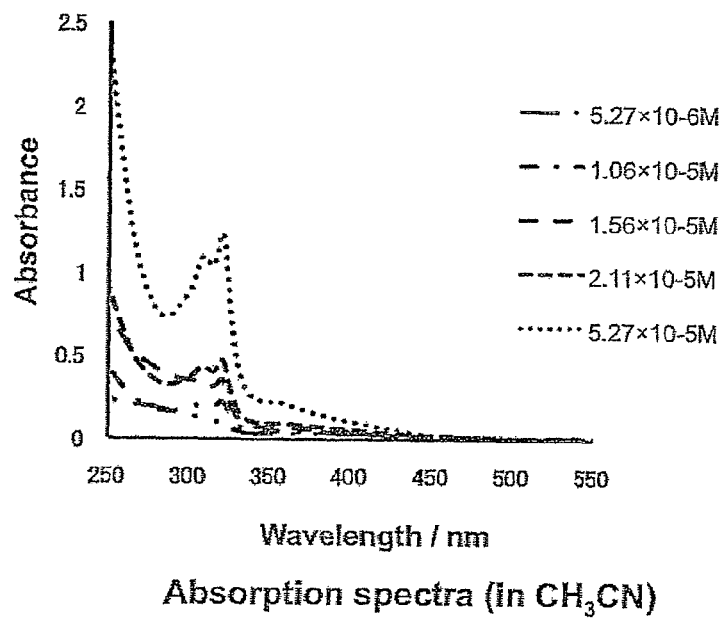
FIG. 13 shows UV-vis absorption spectra of solutions of [Pt$_2$Ag$_2$(bpy)$_2$(3-$^t$Bupz)$_4$](PF$_6$)$_2$ in acetonitrile (concentration of metal complex: 5.27×10$^{-6}$M, 1.06×10$^{-5}$M, 1.56×10$^{-5}$M, 2.11×10$^{-5}$M, 5.27×10$^{-5}$M).
Figure 14:
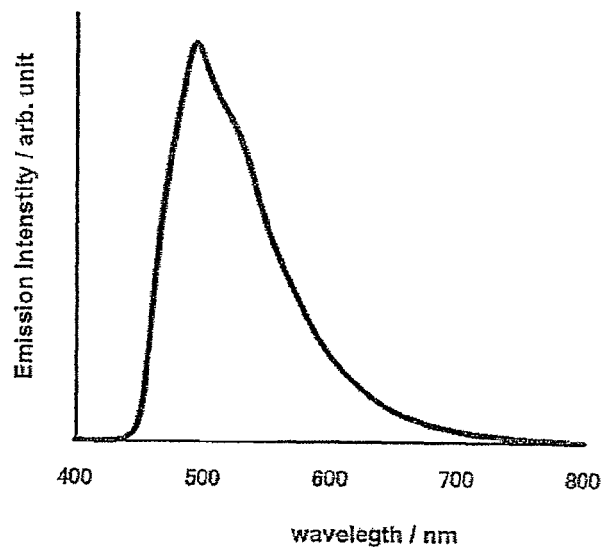
FIG. 14 shows an emission spectrum of [Pt$_2$Ag$_2$(bpy)$_2$(3-$^t$Bupz)$_4$](PF$_6$)$_2$ in a solid state (measurement temperature: 298K).

The emission properties of the metal complex $[Pt_2Ag_2(bpy)_2(3\text{-}^tBupz)_4](PF_6)_2$ are now explained. The UV-vis absorption spectra of the acetonitrile solutions of the metal complex and emission spectrum thereof in a solid state were measured. The UV-vis absorption spectra of the acetonitrile solutions are shown in FIG. 13, and the emission spectrum in the solid state is shown in FIG. 14.

A $5.27 \times 10^{-5}$ M solution of $[Pt_2Ag_2(bpy)_2(3\text{-}^tBupz)_4](PF_6)_2$ in acetonitrile shows two absorption maxima at around 300 nm-350 nm and a broad absorption band at 350 nm-450 nm. The absorption spectrum of a dilute solution does not follow Beer's low, and therefore, the dissociation equilibrium of the $Pt_2Ag_2$ complex is considered to occur at low concentrations. When the metal complex in a solid state was excited with 355 nm UV light at 298K, a spectrum having an emission maximum at 494 nm and a slight vibrational structure was obtained. The emission quantum yield (Φ) of the metal complex in a solid state was 0.51.

Moreover, the emission decay curve of this metal complex in a solid state was measured at 80K, and this was analyzed using a monoexponential function to give the value of i=11.03 μs. The emission decay curve of this metal complex in a solid state was deformed with rising measurement temperature. The emission decay curve measured at 298K was analyzed using a biexponential function $(I(t)=A_1\exp(-t/\tau_1)+A_2\exp(-t/\tau_2))$ to give the values of $\tau_1=1.46$ μs, $A_1=0.12$, $\tau_2=7.87$ μs and $A_2=0.88$. The emission lifetime of this metal complex is comparatively long and the emission is considered to occur from a triplet excited state (i.e., phosphorescence).

Example 7

$[Pt_2Au_2(bpy)_2(3\text{-}^tBupz)_4](PF_6)_2$, which is one kind of the metal complex of the present invention, was synthesized. This metal complex has a constitution wherein, in the above-mentioned formula (C1), $M^{II}$ is $Pt^{II}$, $M^I$ is $Au^I$, $L_C$ is bpy, $L_B$ is 3-$^t$Bupz, and the counter anion is $PF_6^-$.

First, a mononuclear complex $[Pt(bpy)(3\text{-}^tBupzH)_2](PF_6)_2$ was synthesized as an intermediate material in the same manner as in the method explained in Example 5.

Then, using the mononuclear complex $[Pt(bpy)(3\text{-}^tBupzH)_2](PF_6)_2$, which is an intermediate material, a metal complex $[Pt_2Au_2(bpy)_2(3\text{-}^tBupz)_4](PF_6)_2$ was synthesized. $AuCl(SC_4H_8)$ (19 mg, 0.06 mmol) and triethylamine (18 μL, 0.11 mmol) were added to a solution (10 mL) of $[Pt(bpy)(3\text{-}^tBupzH)_2](PF_6)_2$ (41 mg, 0.06 mmol) in acetonitrile, and the mixture was stirred at room temperature for 1 hr. At this time, the white-yellow reaction solution changed to a yellow solution. This yellow solution was concentrated, the precipitated yellow solid was collected, washed with water and methanol, and dried under reduced pressure. The yield was 12 mg, 20%. This reaction can be shown by the following chemical reaction formula.

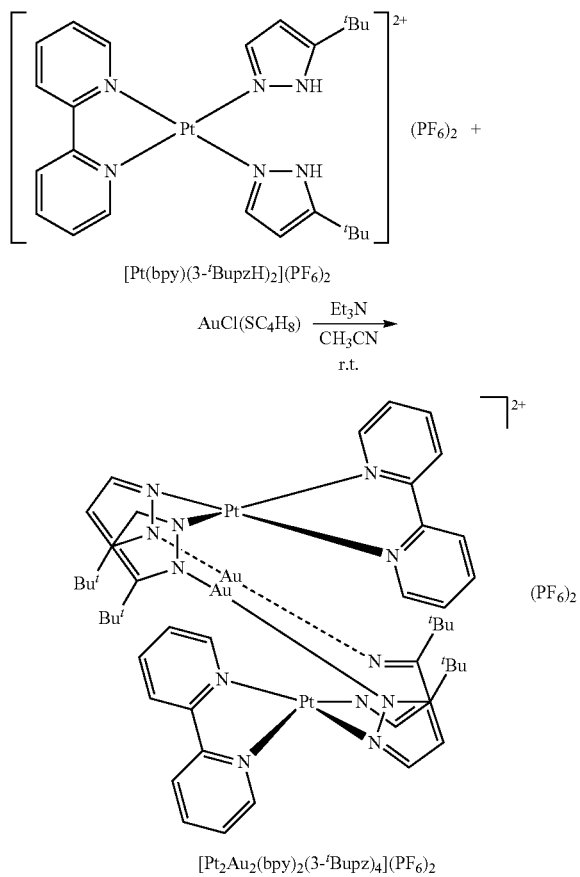

Furthermore, recrystallization from acetonitrile/methanol was performed to give a single crystal. The obtained metal complex emitted yellow light under irradiation of UV light (365 nm). This metal complex was readily soluble in hexane, dichloromethane, ethanol, acetonitrile and acetone, soluble in diethyl ether, chloroform, methanol, benzene and DMSO, and hardly soluble in water.

Furthermore, the product was identified by IR and $^1$H NMR spectra.

The results of identification by IR spectrum are as follows.
IR(KBr): 3420 (w), 2956 (m), 2676 (m), 2606 (m), 2498 (s), 2360 (s), 1610 (s), 1475 (s), 1454 (s), 1397 (s), 1251 (m), 1210 (m), 1174 (m), 11036 (m), 843 (m), 771 (s), 723 (s), 558 (s), 279 (s)

The results of identification by $^1$H NMR spectrum are as shown in the following Table 14. Each item in Table 14 is as defined in Table 1.

TABLE 14

$^1$H NMR data of [Pt$_2$Au$_2$(bpy)$_2$(3-$^t$Bupz)$_4$](PF$_6$)$_2$
(in CD$_3$CN, TMS, 300 MHz)

| δ (ppm) | Shape(J/Hz) | Int. | Assign. |
|---|---|---|---|
| 8.40 | dd (1.4, 1.7) | 1 | H6 of bpy |
| 8.39 | d (0.9) | 1 | H3 of bpy |

TABLE 14-continued $^1$H NMR data of [Pt$_2$Au$_2$(bpy)$_2$(3-$^t$Bupz)$_4$](PF$_6$)$_2$
(in CD$_3$CN, TMS, 300 MHz)

| δ (ppm) | Shape(J/Hz) | Int. | Assign. |
|---|---|---|---|
| 8.19 | d (5.6) | 1 | H4 of bpy |
| 7.77 | ddd (3.2, 5.8, 3.2) | 1 | H5 of bpy |
| 7.55 | d (2.3) | 1 | H5 of 3-$^t$Bupz |
| 6.16 | d (2.3) | 1 | H4 of 3-$^t$Bupz |
| 0.99 | s | 9 | $^t$Bu of 3-$^t$Bupz |

Furthermore, mass spectrometry was performed by the FAB-MS method. The results are as follows.
FAB-MS: m/z=1536 [M-PF$_6$]$^+$ The structure of the obtained metal complex is explained. The molecular structure of the obtained metal complex was determined by single crystal X-ray structural analysis. The crystallographic data are shown in Table 15. Here, each item in Table 15 is as defined in Table 6.

TABLE 15

Crystallographic data for
[Pt$_2$Au$_2$(bpym)$_2$(3-$^t$Bupz)$_4$](PF$_6$)$_2$·CH$_3$CN

| | |
|---|---|
| Empirical Formula | C$_{52}$H$_{66}$Au$_2$F$_{12}$N$_{14}$P$_2$Pt$_2$ |
| Fw | 1961.23 |
| T, K | 93 |
| λ, Å | 0.71075 |
| Cryst Syst | monoclinic |
| Space Group | C2/c (# 15) |
| a, Å | 20.910(4) |
| b, Å | 13.559(3) |
| c, Å | 21.496(5) |
| β, deg | 95.118(3) |
| V, Å$^3$ | 6070 (2) |
| Z | 4 |
| ρ$_{calcd}$, g cm$^{-3}$ | 2.146 |
| μ(Mo Kα), cm$^{-1}$ | 95.503 |
| No. of Reflections Measured | Unique: 6898 (R$_{int}$ = 0.0493) |
| Residuals: R; Rw | 0.0748; 0.1676 |
| Residuals: R1 | 0.0639 |
| GOF | 1.111 |

Figure 15:
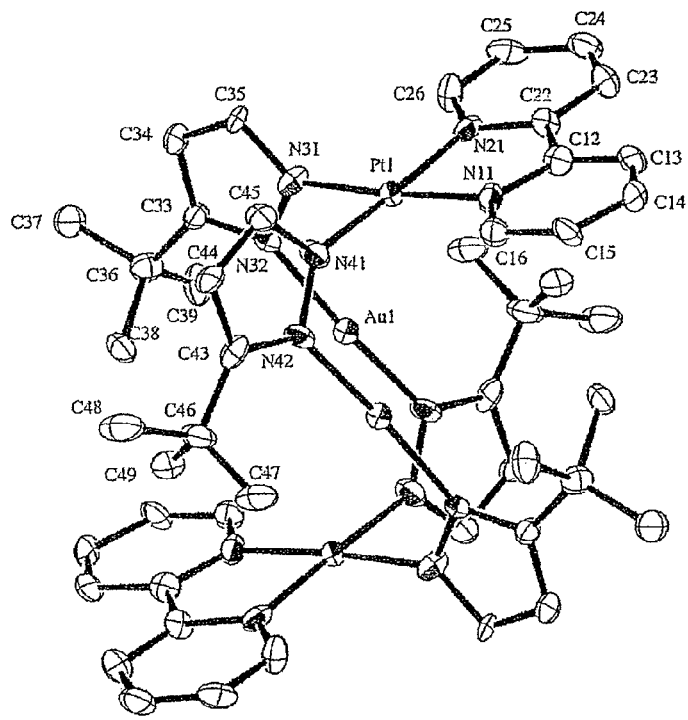
FIG. 15 is an ORTEP diagram showing the structure of a cation in [Pt$_2$Au$_2$(bpy)$_2$(3-$^t$Bupz)$_4$](PF$_6$)$_2$.

In addition, the structure of cation in this metal complex is shown in the ORTEP diagram of FIG. 15. This metal complex was crystallized into a form containing acetonitrile. As shown in FIG. 15, two Pt atoms and two Au atoms are contained in this cation. A crystallographically imposed center of symmetry is located at the midpoint between Au . . . Au, and a half of the atoms in the crystals is independent. 2,2'-Bipyridine (bpy) coordinates as a bidentate chelating ligand to each Pt atom, and two 3-t-butylpyrazolato ligands (3-$^t$Bupz) coordinate with N atom located farther from t-butyl group to the residual coordination site. Each Pt atom forms a {(bpy)Pt(3-$^t$Bupz)$_2$} unit, and two 3-$^t$Bupz ligands of each unit coordinate to different Au atoms, whereby a 12-membered ring containing two Pt atoms and two Au atoms is formed. In [Pt$_2$Au$_2$(bpy)$_2$(3-$^t$Bupz)$_4$](PF$_6$)$_2$, the Pt . . . Pt distance is 6.3288(11) Å, the Pt . . . Au distances are 3.4904(8) and 3.6463(9) Å, and the Au . . . Au distance is 3.3020(8) Å. The Pt—N distances are within the range of 1.994(10)-2.011(10) Å, and the Au—N distances are 2.004(9) Å and 2.025(8) Å.

Figure 16:
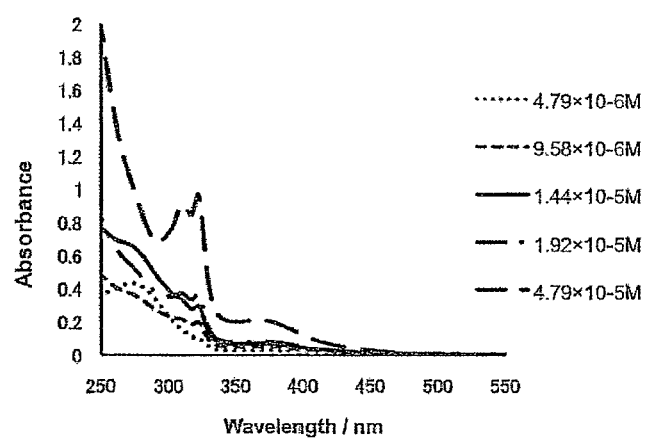
FIG. 16 shows UV-vis absorption spectra of solutions of [Pt$_2$Au$_2$(bpy)$_2$(3-$^t$Bupz)$_4$](PF$_6$)$_2$ in acetonitrile (concentration of metal complex: 4.79×10$^{-6}$M, 9.58×10$^{-6}$M, 1.44×10$^{-5}$M, 1.92×10$^{-5}$M, 4.79×10$^{-5}$M)
Figure 17:
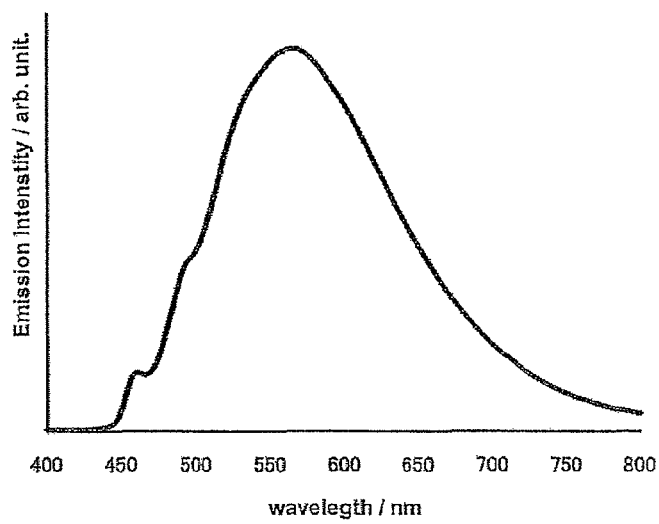
FIG. 17 shows an emission spectrum of [Pt$_2$Au$_2$(bpy)$_2$(3-$^t$Bupz)$_4$](PF$_6$)$_2$ in a solid state (measurement temperature: 298K).

The emission properties of the metal complex [Pt$_2$Au$_2$(bpy)$_2$(3-$^t$Bupz)$_4$](PF$_6$)$_2$ are now explained. The UV-vis absorption spectra of the acetonitrile solutions of the metal complex and emission spectrum thereof in a solid state were measured. The UV-vis absorption spectrum of the acetonitrile solutions are shown in FIG. 16, and the emission spectrum in the solid state is shown in FIG. 17.

A 4.79×10$^{-5}$M solution of [Pt$_2$Au$_2$(bpy)$_2$(3-$^t$Bupz)$_4$](PF$_6$)$_2$ in acetonitrile shows two absorption maxima at around 300 nm-350 nm and a broad absorption band at 350 nm-450 nm. The absorption spectrum of a dilute solution does not follow Beer's low, and therefore, the dissociation equilibrium of the Pt$_2$Au$_2$ complex is considered to occur at low concentrations. When the metal complex in a solid state was excited with 355 nm UV light at 298K, a spectrum having an emission maximum at 569 nm and a slight vibrational structure was obtained. The emission quantum yield (Φ) of the metal complex in a solid state was 0.029.

Moreover, the emission decay curve of this metal complex in a solid state was measured, and analyzed using a biexponential function (I(t)=A$_1$exp(-t/τ$_1$)+A$_2$exp(-t/τ$_2$)) to give the values of τ$_1$=0.08 is, A$_1$=0.54, τ$_2$=0.48 μs and A$_2$=0.46 (measurement temperature: 298K). The emission lifetime of this metal complex is comparatively long and the emission is considered to occur from a triplet excited state (i.e., phosphorescence).

Example 8

[Pt$_2$Cu$_2$(bpy)$_2$(3-$^t$Bupz)$_4$](PF$_6$)$_2$, which is one kind of the metal complex of the present invention, was synthesized. This metal complex has a constitution wherein, in the above-mentioned formula (C1), M$^{II}$ is Pt$^{II}$, M$^I$ is Cu$^I$, L$_C$ is bpy, L$_B$ is 3-$^t$Bupz, and the counter anion is PF$_6^-$.

First, a mononuclear complex [Pt(bpy)(3-$^t$BupzH)$_2$](PF$_6$)$_2$ was synthesized as an intermediate material in the same manner as in the method explained in Example 5.

Then, using the mononuclear complex [Pt(bpy)(3-$^t$BupzH)$_2$](PF$_6$)$_2$, which is an intermediate material, a metal complex [Pt$_2$Cu$_2$(bpy)$_2$(3-$^t$Bupz)$_4$](PF$_6$)$_2$ was synthesized.

[Cu(CH$_3$CN)$_4$](BF$_4$) (11 mg, 0.035 mmol) and triethylamine (23 μL, 0.14 mmol) were added to a solution (10 mL) of [Pt(bpy)(3-$^t$BupzH)$_2$](PF$_6$)$_2$ (32 mg, 0.036 mmol) in acetonitrile, and the mixture was stirred at room temperature for 2 hr. After the reaction, the yellow reaction solution was concentrated, and the yellow precipitate resulting from the concentration was collected, washed with water and methanol, and dried under reduced pressure. The yield was 34 mg, 16%. This reaction can be shown by the following chemical reaction formula.

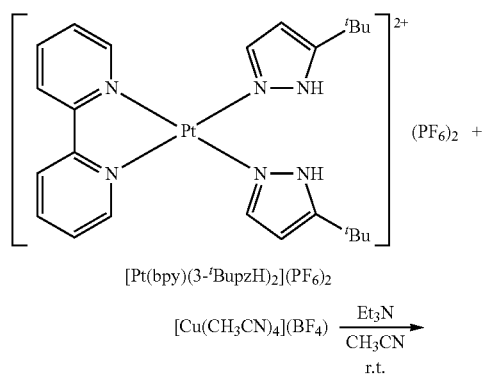

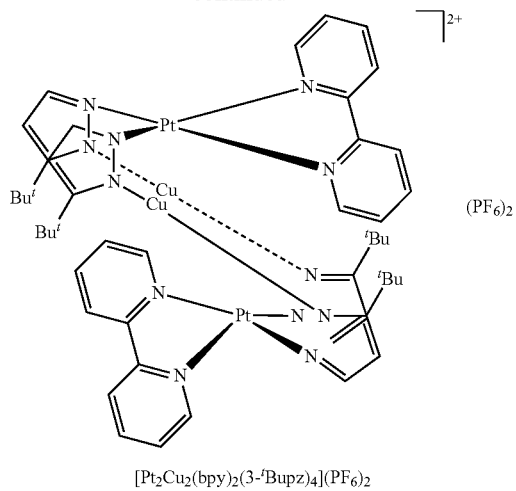

The obtained metal complex was readily soluble in dichloromethane, methanol, DMSO and benzene, soluble in chloroform, and hardly soluble in diethyl ether, ethanol, water and hexane.

Furthermore, the product was identified by IR and $^1$H NMR spectra.

The results of identification by IR spectrum are as follows.

IR(KBr): 3125 (w), 2948 (m), 2360 (s), 2342 (m), 1610 (s), 1485 (s), 1455 (s), 1428 (m), 1395 (s), 1360 (m), 1324 (s), 1249 (s), 1179 (m), 1084 (m), 844 (m), 774 (s), 726 (s), 655 (w), 558 (s), 279 (s)

The results of identification by $^1$H NMR spectrum are as shown in the following Table 16. Each item in Table 16 is as defined in Table 1.

TABLE 16

$^1$H NMR data of [Pt$_2$Cu$_2$(bpy)$_2$(3-$^t$Bupz)$_4$](PF$_6$)$_2$
(in CD$_3$CN, TMS, 400 MHz, -50° C.)

| δ (ppm) | Shape(J/Hz) | Int. | Assign. |
|---|---|---|---|
| 8.33 | m | 2 | H6, H3 of bpy |
| 7.80 | dd (5.4) | 1 | H4 of bpy |
| 7.62 | ddd (1.5, 5.4, 7.5) | 1 | H5 of bpy |
| 7.43 | d (2.0) | 1 | H5 of 3-$^t$Bupz |
| 6.21 | d (2.0) | 1 | H4 of 3-$^t$Bupz |
| 1.39 | s | 9 | $^t$Bu of 3-$^t$BupzH |

Furthermore, mass spectrometry was performed by the FAB-MS method. The results are as follows.

FAB-MS: m/z=1466 [M-PF$_6$]$^+$

Figure 18:
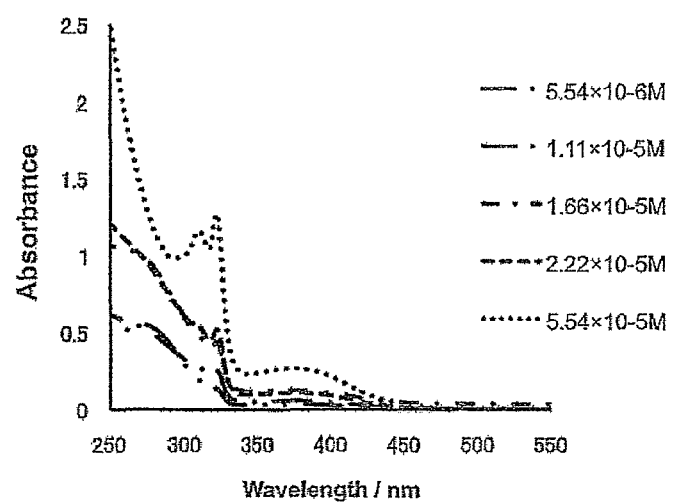
FIG. 18 shows UV-vis absorption spectra of solutions of [Pt$_2$Cu$_2$(bpy)$_2$(3-$^t$Bupz)$_4$](PF$_6$)$_2$ in acetonitrile (concentration of metal complex: 5.54×10$^{-6}$M, 1.11×10$^{-5}$M, 1.66×10$^{-5}$M, 2.22×10$^{-5}$M, 5.54×10$^{-5}$M).
Figure 19:
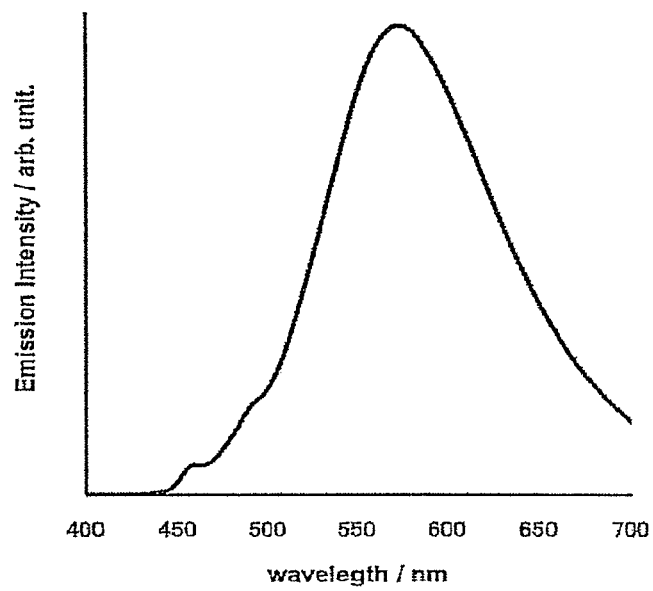
FIG. 19 shows an emission spectrum of [Pt$_2$Cu$_2$(bpy)$_2$(3-$^t$Bupz)$_4$](PF$_6$)$_2$ in a solid state (measurement temperature: 298K).

The emission properties of the metal complex [Pt$_2$Cu$_2$(bpy)$_2$(3-$^t$Bupz)$_4$](PF$_6$)$_2$ are now explained. The UV-vis absorption spectra of the acetonitrile solutions of the metal complex and emission spectrum thereof in a solid state were measured. The UV-vis absorption spectra of the acetonitrile solutions are shown in FIG. 18, and the emission spectrum in the solid state is shown in FIG. 19.

A 5.54×10$^{-5}$M solution of [Pt$_2$Cu$_2$(bpy)$_2$(3-$^t$Bupz)$_4$](PF$_6$)$_2$ in acetonitrile shows two absorption maxima at around 300 nm-350 nm and a broad absorption band at 350 nm-450 nm. The absorption spectrum of a dilute solution does not follow Beer's low, and therefore, the dissociation equilibrium of the Pt$_2$Cu$_2$ complex is considered to occur at low concentrations. When the metal complex in a solid state was excited with 355 nm UV light at 298K, a spectrum having an emission maximum at 575 nm was obtained. The emission quantum yield (Φ) of the metal complex in a solid state was 0.025.

Moreover, the emission decay curve of this metal complex in a solid state was measured, and analyzed using a biexponential function (I(t)=$A_1$exp(−t/$τ_1$)+$A_2$exp(−t/$τ_2$)) to give the values of $τ_1$=0.04 μs, $A_1$=0.61, $τ_2$=0.14 μs and $A_2$=0.39 (measurement temperature: 298K). The emission lifetime of this metal complex is comparatively long and the emission is considered to occur from a triplet excited state (i.e., phosphorescence).

Example 9

[$Pt_2Ag_2$(bpy)$_2$(3-$^t$Bupz)$_4$](BF$_4$)$_2$, which is one kind of the metal complex of the present invention, was synthesized. This metal complex has a constitution wherein, in the above-mentioned formula (C1), $M^{II}$ is $Pt^{II}$, $M^I$ is $Ag^+$, $L_C$ is bpy, $L_B$ is 3-$^t$Bupz, and the counter anion is BF$_4$—.

First, a mononuclear complex [Pt(bpy)(3-$^t$BupzH)$_2$](BPh$_4$)$_2$, which is an intermediate material, was synthesized. To be specific, [PtCl$_2$(bpy)] (40 mg, 0.10 mmol) and 3-$^t$BupzH (40 mg, 0.32 mmol) were stirred in water (5 mL) with heating at 80° C. for 4 hr. At this time, the orange suspension changed to a yellow solution. When NaBPh$_4$ (140 mg, 0.45 mmol) was added to this yellow solution, white-yellow precipitate was deposited. The precipitate was collected by filtration, washed with water and dried under reduced pressure. The yield was 90 mg, 90%. This reaction can be shown by the following chemical reaction formula.

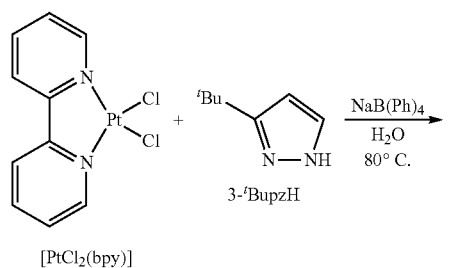

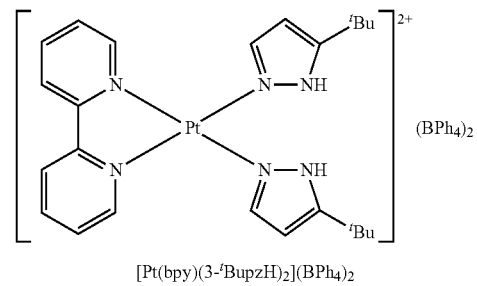

[Pt(bpy)(3-$^t$BupzH)$_2$](BPh$_4$)$_2$

The obtained metal complex was readily soluble in DMSO, methanol, acetone, acetonitrile and dichloromethane, soluble in hexane, toluene, chloroform and THF, and insoluble in diethyl ether, ethanol and water.

Furthermore, the product was identified by IR and $^1$H NMR spectra.

The results of identification by IR spectrum are as follows.

IR(KBr): 3054 (m), 2965 (m), 2360 (w), 2342 (w), 1608 (w), 1578 (w), 1476 (s), 1453 (m), 1370 (s), 1264 (s), 1245 (s), 1249 (s), 1130 (m), 733 (s), 705 (s)

The results of identification by $^1$H NMR spectrum are as shown in the following Table 17. Each item in Table 17 is as defined in Table 1.

TABLE 17

$^1$H NMR data of [Pt(bpy)(3-$^t$BupzH)$_2$](BPh$_4$)$_2$ (in CD$_3$CN, TMS, 300 MHz)

| δ (ppm) | Shape (J/Hz) | Int. | Assign. |
|---|---|---|---|
| 8.30 | dt (8.5, 7.8, 1.4) | 1H | H6 of bpy |
| 8.27 | dd (8.5, 1.4) | 1H | H3 of bpy |
| 7.74 | d (2.2) | 1H | H5 of bpy |
| 7.63 | m | 1H | H4 of bpy |
| 7.26 | m | 8H | Ph of BPh$_4$ |
| 7.15 | m | 1H | H5 of 3-$^t$BupzH |
| 6.97 | t (7.5) | 8H | Ph of BPh$_4$ |
| 6.82 | t (7.3) | 4H | Ph of BPh$_4$ |
| 6.41 | d (2.2) | 1H | H4 of 3-$^t$BupzH |
| 1.31 | s | 9H | $^t$Bu of 3-$^t$BupzH |

Then, using a mononuclear complex [Pt(bpy)(3-$^t$BupzH)$_2$](BPh$_4$)$_2$r which is an intermediate material, a metal complex [Pt$_2$Ag$_2$(bpy)$_2$(3-$^t$Bupz)$_4$](BF$_4$)$_2$ was synthesized. To be specific, AgBF$_4$ (10.1 mg, 0.05 mmol) and Et$_3$N (33 μL, 0.2 mmol) were added to a solution (10 mL) of [Pt(bpy)(3-$^t$BupzH)$_2$](BPh$_4$)$_2$ (60.0 mg, 0.05 mmol) in methanol, and the mixture was stirred under shading at room temperature for 3 hr. The reaction solution changed from a yellow solution to a pale-yellow suspension. The suspension was concentrated in an evaporator. The precipitated yellow-white solid was collected by filtration, washed with hexane and dried under reduced pressure. The yield was 13.8 mg, 35%. This reaction can be shown by the following chemical reaction formula.

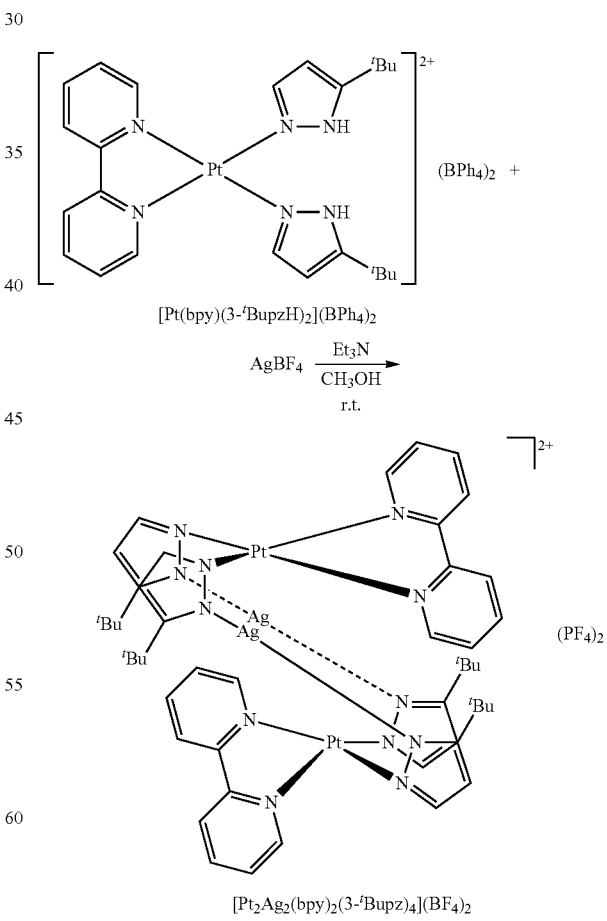

[Pt$_2$Ag$_2$(bpy)$_2$(3-$^t$Bupz)$_4$](BF$_4$)$_2$

This metal complex exhibited green emission under irradiation of UV light (365 nm). This metal complex was readily soluble in acetonitrile, acetone, methanol, ethanol, toluene and DMSO, soluble in chloroform, methylene chloride and THF, and hardly soluble in hexane, diethyl ether and water.

Furthermore, the product was identified by IR and $^1$H NMR spectra.

The results of identification by IR spectrum are as follows.

IR(KBr): 3452 (w), 2957 (m), 2360 (m), 1610 (s), 1492 (m), 1473 (s), 1361 (m), 1328 (s), 1163 (s), 1136 (s), 1075 (m), 844 (m), 772 (s), 558 (s), 503 (m), 421 (m)

The results of identification by $^1$H NMR spectrum are as shown in the following Table 18. Each item in Table 18 is as defined in Table 1.

TABLE 18

$^1$H NMR data of [Pt$_2$Ag$_2$(bpy)$_2$(3-$^t$Bupz)$_4$](BF$_4$)$_2$ (in CDCl$_3$, TMS, 300 MHz)

| δ (ppm) | Shape(J/Hz) | Int. | Assign. |
|---|---|---|---|
| 8.40 | s | 2H | H6, H3 of bpy |
| 8.04 | s | 1H | H4 of bpy |
| 7.76 | s | 1H | H5 of bpy |
| 7.54 | s | 1H | H5 of 3-$^t$Bupz |
| 6.15 | s | 1H | H4 of 3-$^t$Bupz |
| 0.90 | s | 9H | $^t$Bu of 3-$^t$Bupz |

Furthermore, mass spectrometry was performed by the FAB-MS method. The results are as follows.

FAB-MS: m/z=1497.3 [M-BF$_4$]$^+$

Figure 20:
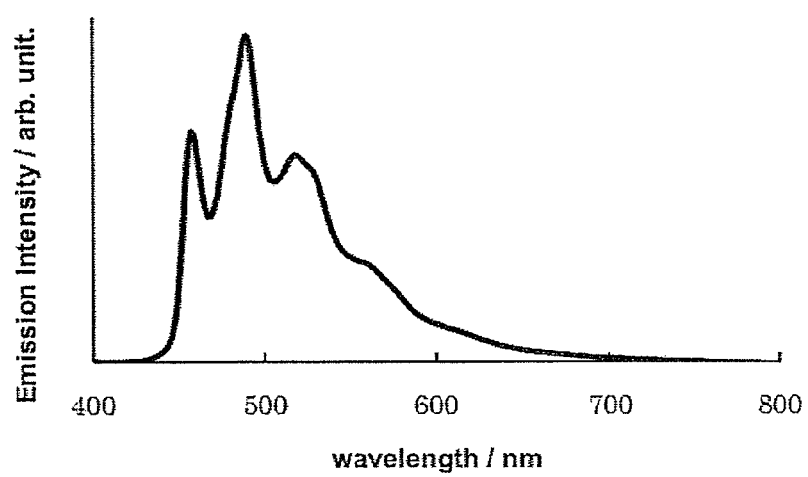
FIG. 20 shows an emission spectrum of [Pt$_2$Ag$_2$(bpy)$_2$(3-$^t$Bupz)$_4$](BF$_4$)$_2$ in a solid state (measurement temperature: 298K).

The emission properties of the metal complex [Pt$_2$Ag$_2$(bpy)$_2$(3-$^t$Bupz)$_4$](BF$_4$)$_2$ are now explained. The emission spectrum of the metal complex in a solid state was measured. The emission spectrum is shown in FIG. 20.

When the [Pt$_2$Ag$_2$(bpy)$_2$(3-$^t$Bupz)$_4$](BF$_4$)$_2$ in a solid state was excited with 355 nm UV light at 298K, an emission spectrum with a vibrational structure having emission maxima at 458 nm, 489 nm and 517 nm was obtained. The emission quantum yield (Φ) of the metal complex in a solid state was 0.55.

Moreover, the emission decay curve of this metal complex in a solid state was measured, and analyzed using a biexponential function (I(t)=A$_1$exp(−t/τ$_1$)+A$_2$exp(−t/τ$_2$)) to give the values of τ$_1$=0.26 μs, A$_1$=0.35, τ$_2$=10.23 μs and A$_2$=0.65 (measurement temperature: 298K). The emission lifetime of this metal complex is comparatively long and the emission is considered to occur from a triplet excited state (i.e., phosphorescence).

Example 10

[Pt$_2$(5,5'-dmbpy)$_2$(3-$^t$Bupz)$_2$(3-$^t$BupzH)$_2$](PF$_6$)$_2$, which is one kind of the metal complex of the present invention, was synthesized. This metal complex has a constitution wherein, in the above-mentioned formula (C1), M$^{II}$ is Pt$^{II}$, M$^I$ is H$^+$, L$_C$ is 5,5' dmbpy, L$_B$ is 3-$^t$Bupz, and the counter anion is PF$_6^-$. Two H$^+$ and two 3-$^t$Bupz are bonded to form two 3-$^t$BupzH. The 5,5'-dmbpy is 5,5'-dimethyl-2,2'-bipyridine.

First, a mononuclear complex [Pt(5,5'-dmbpy)(3-$^t$BupzH)$_2$](PF$_6$)$_2$, which is an intermediate material, was synthesized. To be specific, a solution (5 mL) of 3-$^t$BupzH (41 mg, 0.32 mmol) in water was added to a solution (5 mL) of [PtCl$_2$(5,5-dmbpy)](41 mg, 0.10 mmol) in acetonitrile, and the mixture was stirred with heating at 80° C. for 4 hr. At this time, the yellow suspension changed to a yellow solution. When NH$_4$PF$_6$ (73 mg, 0.45 mmol) was added to this yellow solution, white-yellow precipitate was deposited. This precipitate was collected by filtration, washed with water and dried under reduced pressure. The yield was 62 mg, 67%. This reaction can be shown by the following chemical reaction formula.

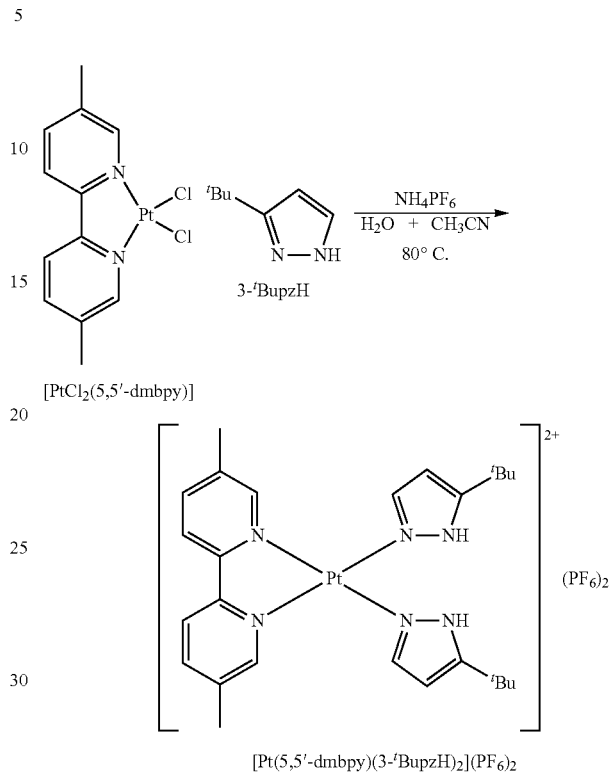

The obtained metal complex was readily soluble in benzene, THF, DMF and DMSO, soluble in methanol, ethanol, acetonitrile and dichloromethane, and insoluble in chloroform, water, hexane, toluene and diethylether.

Furthermore, the product was identified by IR spectrum.

The results of identification by IR spectrum are as follows.

IR(KBr): 3427 (m), 3125 (m), 3021 (m), 2965 (s), 2913 (m), 2828 (s), 2359 (m), 1609 (m), 1569 (s), 1486 (s), 1393 (s), 1294 (s), 1133 (s), 1069 (s), 990 (s), 841 (s), 558 (s)

Furthermore, mass spectrometry was performed by the ESI-MS method. The results are as follows.

ESI-MS: m/z=626 [M-PF$_6$]$^+$

Then, using a mononuclear complex [Pt(5,5'-dmbpy)(3-$^t$BupzH)$_2$](PF$_6$)$_2$r which is an intermediate material, a metal complex [Pt$_2$(5,5'-dmbpy)$_2$(3-$^t$Bupz)$_2$(3-$^t$BupzH)$_2$](PF$_6$)$_2$ was synthesized. To be specific, KOH (2 equivalents) was added to a solution (10 mL) of [Pt(5,5'-dmbpy)(3-$^t$BupzH)$_2$](PF$_6$)$_2$ (43 mg, 0.05 mmol) in methanol, and the mixture was stirred at room temperature for 3 hr. The reaction solution changed from white-yellow to yellow. This solution was concentrated to dryness. The obtained yellow solid was dissolved in acetonitrile, and unreacted KOH was filtered off. The yellow filtrate was concentrated to dryness. The obtained solid was dissolved in dichloromethane, and hexane was added to this solution. The precipitated yellow solid was collected, washed with hexane and dried under reduced pressure. The yield was 29.5 mg, 81%. This reaction can be shown by the following chemical reaction formula.

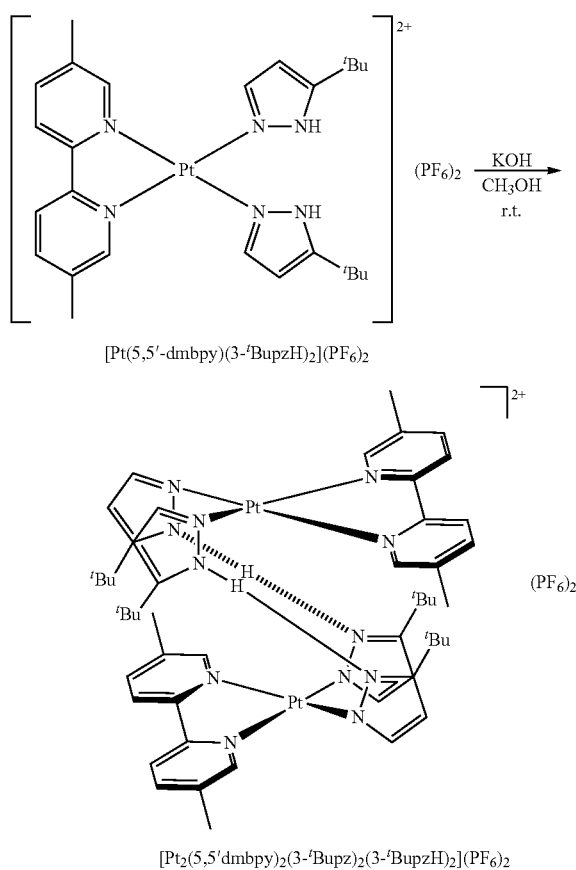

[Pt(5,5'-dmbpy)(3-ᵗBupzH)₂](PF₆)₂

[Pt₂(5,5'dmbpy)₂(3-ᵗBupz)₂(3-ᵗBupzH)₂](PF₆)₂

This metal complex exhibited yellow emission under irradiation of UV light (365 nm). This metal complex was readily soluble in THF, acetone, methanol, ethanol, dichloromethane, chloroform and DMF, soluble in benzene, diethyl ether, acetonitrile and DMSO, and insoluble in toluene and water.

Furthermore, the product was identified by IR and ¹H NMR spectra.

The results of identification by IR spectrum are as follows.

IR(KBr): 3391 (w), 2958 (s), 2360 (m), 2139 (m), 1484 (s), 1387 (m), 1360 (w), 1237 (s), 1045 (m), 840 (s), 754 (m), 503 (w)

The results of identification by ¹H NMR spectrum are as shown in the following Table 19. Each item in Table 19 is as defined in Table 1.

TABLE 19

¹H NMR data of [Pt₂(5,5'-dmbpy)(3-ᵗBupz)₂(3-ᵗBupzH)₂](PF₆)₂
(in CDCl₃, TMS, 300 MHz)

| δ (ppm) | Shape(J/Hz) | Int. | Assign. |
|---|---|---|---|
| 9.09 | s | 1H | H6 of 5,5'-dmbpy |
| 7.83 | s | 1H | H3 of 5,5'-dmbpy |
| 7.24 | s | 1H | H4 of 5,5'-dmbpy |
| 7.00 | s | 1H | H5 of 3-ᵗBupz |
| 6.01 | s | 1H | H4 of 3-ᵗBupz |
| 2.40 | s | 3H | Me of 5,5'-dmbpy |
| 1.42 | s | 9H | ᵗBu of 3-ᵗBupz |

Furthermore, mass spectrometry was performed by the FAB-MS method. The results are as follows.

FAB-MS: m/z=1251.6 [M-PF₆]⁺

Figure 21:
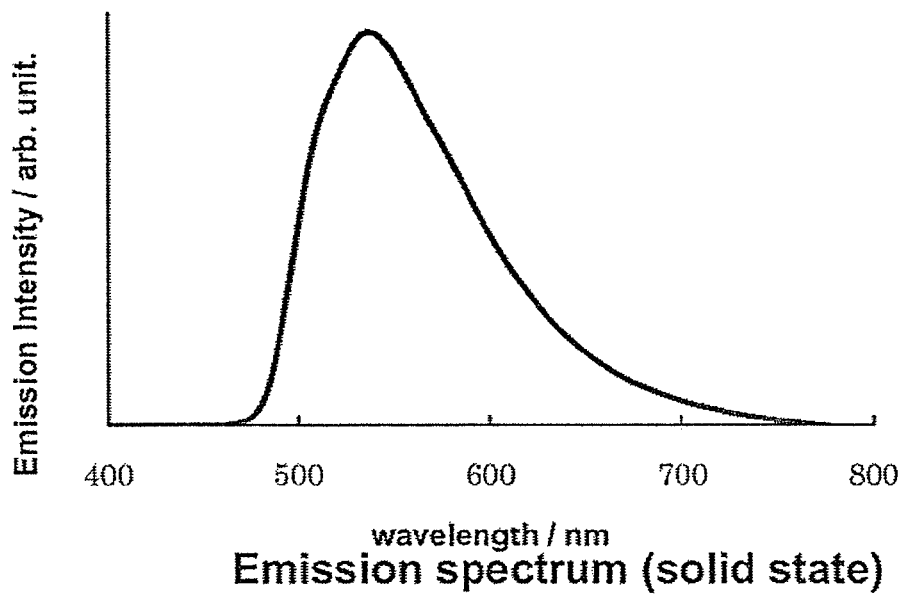
FIG. 21 shows an emission spectrum of [Pt$_2$(5,5'-dmbpy)$_2$(3-$^t$Bupz)$_2$(3-$^t$BupzH)$_2$](PF$_6$)$_2$ in a solid state (measurement temperature: 298K).

The emission properties of the metal complex [Pt₂(5,5'-dmbpy)₂(3-ᵗBupz)₂(3-ᵗBupzH)₂](PF₆)₂ are now explained. The emission spectrum of the metal complex in a solid state was measured. The emission spectrum is shown in FIG. 21.

When the [Pt₂(5,5'-dmbpy) 2(3-ᵗBupz)₂(3-ᵗBupzH)₂] (PF₆)₂ in a solid state was excited with 355 nm UV light at 298K, a broad spectrum showing an emission maximum at 536 nm was obtained. The emission quantum yield (Φ) in a solid state was 0.09.

Moreover, the emission decay curve of this metal complex in a solid state was measured, and analyzed using a biexponential function $(I(t)=A_1\exp(-t/\tau_1)+A_2\exp(-t/\tau_2))$ to give the values of $\tau_1=0.32$ μs, $A_1=0.49$, $\tau_2=0.75$ μs and $A_2=0.51$ (measurement temperature: 298K). The emission lifetime of this metal complex is comparatively long and the emission is considered to occur from a triplet excited state (i.e., phosphorescence).

Example 11

[Pt₂Ag₂(5,5'-dmbpy)₂(3-ᵗBupz)₄](PF₆)₂, which is one kind of the metal complex of the present invention, was synthesized. This metal complex has a constitution wherein, in the above-mentioned formula (C1), $M^{II}$ is $Pt^{II}$, $M^I$ is $Ag^I$, $L_C$ is 5,5'-dmbpy, $L_B$ is 3-ᵗBupz, and the counter anion is $PF_6^-$.

First, a mononuclear complex [Pt(5,5'-dmbpy)(3-ᵗBupzH)₂](PF₆)₂ was synthesized as an intermediate material in the same manner as in the method explained in Example 10.

Then, using the mononuclear complex [Pt(5,5'-dmbpy)(3-ᵗBupzH)₂](PF₆)₂, which is an intermediate material, [Pt₂Ag₂(5,5'-dmbpy)₂(3-ᵗBupz)₄](PF₆)₂ was synthesized. To be specific, AgBF₄ (9.7 mg, 0.05 mmol) and triethylamine (20 μL, 0.12 mmol) were added to a solution of (10 mL) of [Pt(5,5'-dmbpy)(3-ᵗBupzH)₂](PF₆)₂ (40.1 mg, 0.04 mmol) in acetonitrile, and the mixture was stirred under shading at room temperature for 3 hr. At this time, the yellow solution changed to a yellow suspension. The solid was collected by filtration, washed with hexane and dried under reduced pressure. The yield was 43 mg, 61%. This reaction can be shown by the following chemical reaction formula.

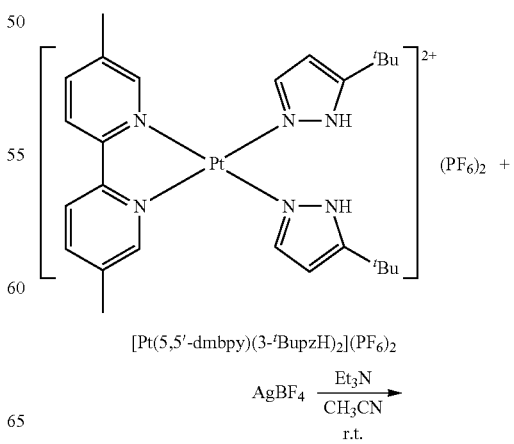

[Pt(5,5'-dmbpy)(3-ᵗBupzH)₂](PF₆)₂

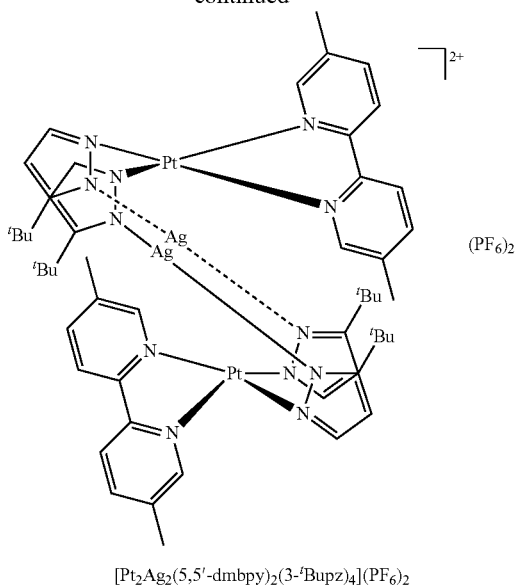

[Pt₂Ag₂(5,5'-dmbpy)₂(3-ᵗBupz)₄](PF₆)₂

This metal complex exhibited blue-green emission under irradiation of UV light (365 nm). This metal complex was readily soluble in acetonitrile and acetone, soluble in dichloromethane and benzene, and insoluble in hexane, diethyl ether, toluene, methanol, ethanol, chloroform and water.

Furthermore, the product was identified by IR and $^1$H NMR spectra.

The results of identification by IR spectrum are as follows.
IR(KBr): 3658 (w), 3436 (w), 2960 (s), 2360 (w), 1609 (s), 1485 (s), 1391 (s), 1329 (s), 1146 (s), 1092 (s), 1018 (s), 839 (s), 770 (m), 558 (s)

The results of identification by $^1$H NMR spectrum are as shown in the following Table 20. Each item in Table 20 is as defined in Table 1.

TABLE 20

$^1$H NMR data of [Pt₂Ag₂(5,5'-dmbpy)₂(3-ᵗBupz)₄](PF₆)₂ (in CD₃CN, TMS, 300 MHz)

| δ (ppm) | Shape(J/Hz) | Int. | Assign. |
|---|---|---|---|
| 8.21 | s | 1H | H6 of 5,5'-dmbpy |
| 8.20 | s | 2H | H3 of 5,5'-dmbpy |
| 7.84 | s | 1H | H4 of 5,5'-dmbpy |
| 7.56 | d (2.3) | 1H | H5 of 3-ᵗBupz |
| 6.17 | d (2.3) | 1H | H4 of 3-ᵗBupz |
| 2.39 | s | 3H | Me of 5,5'-dmbpy |
| 1.01 | s | 9H | ᵗBu of ᵗBupz |

Figure 22:
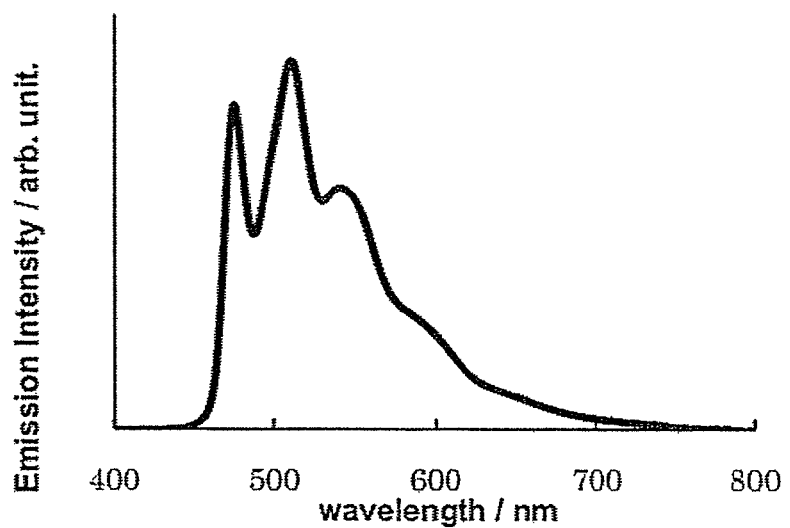
FIG. 22 shows an emission spectrum of [Pt$_2$Ag$_2$(5,5'-dmbpy)$_2$(3-$^t$Bupz)$_4$](PF$_6$)$_2$ in a solid state (measurement temperature: 298K).

The emission properties of the metal complex [Pt₂Ag₂(5,5'-dmbpy)₂(3-ᵗBupz)₄](PF₆)₂ are now explained. The emission spectrum of the metal complex in a solid state was measured. The emission spectrum is shown in FIG. 22.

When [Pt₂Ag₂(5,5'-dmbpy)₂(3-ᵗBupz)₄](PF₆)₂ in a solid state was excited with 355 nm UV light at 298K, a spectrum with a remarkable vibrational structure having emission maxima at 475 nm, 510 nm and 541 nm was obtained. The emission quantum yield (Φ) of the metal complex in a solid state was 0.22.

Moreover, the emission decay curve of this metal complex in a solid state was measured, and analyzed using a biexponential function $(I(t)=A_1\exp(-t/1)+A_2\exp(-t/\tau_2))$ to give the values of $\tau_1=1.88$ μs, $A_1=0.24$, $\tau_2=6.45$ μs and $A_2=0.76$ (measurement temperature: 298K). The emission lifetime of this metal complex is comparatively long and the emission is considered to occur from a triplet excited state (i.e., phosphorescence).

Example 12

[Pt₂(4,4'-dmbpy)₂(3-ᵗBupz)₂(3-ᵗBupzH)²](PF₆)₂, which is one kind of the metal complex of the present invention, was synthesized. This metal complex has a constitution wherein, in the above-mentioned formula (C1), $M^{II}$ is $Pt^{II}$, $M^{I}$ is $H^+$, $L_C$ is 4,4'-dmbpy, $L_B$ is 3-ᵗBupz, and the counter anion is $PF_6^-$. Two $H^+$ and two 3-ᵗBupz are bonded to form two 3-ᵗBupzH. The 4,4'-dmbpy is 4,4'-dimethyl-2,2'-bipyridine.

First, a mononuclear complex [Pt(4,4'-dmbpy)(3-ᵗBupzH)₂](PF₆)₂, which is an intermediate material, was synthesized. To be specific, a solution (5 mL) of 3-ᵗBupzH (40 mg, 0.33 mmol) in water was added to a solution (5 mL) of [PtCl₂(4,4-dmbpy)](41 mg, 0.10 mmol) in acetonitrile, and the mixture was stirred with heating at 80° C. for 4 hr. At this time, the yellow suspension changed to a yellow solution. When NH₄PF₆ (73 mg, 0.45 mmol) was added to this yellow solution, white-yellow precipitate was deposited. This precipitate was collected by filtration, washed with water and dried under reduced pressure. The yield was 51 mg, 56%. This reaction can be shown by the following chemical reaction formula.

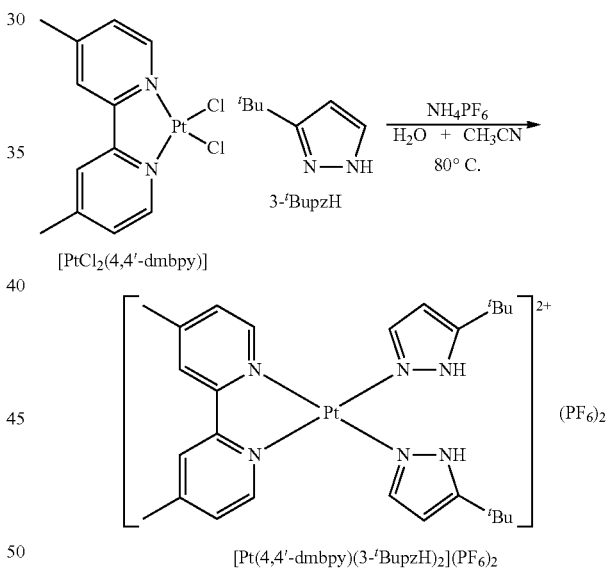

The obtained metal complex was readily soluble in THF and DMF, soluble in acetonitrile, dichloromethane, chloroform, acetone and DMSO, and insoluble in water, methanol, ethanol, hexane, toluene, benzene and diethylether.

Furthermore, the product was identified by IR spectrum. The results of identification by IR spectrum are as follows.
IR(KBr): 3132 (m), 3021 (m), 2966 (s), 2360 (s), 2337 (s), 1621 (s), 1489 (s), 1370 (s), 1132 (s), 991 (s), 848 (s), 558 (s)

Furthermore, mass spectrometry was performed by the FAB-MS method. The results are as follows.
FAB-MS: m/z=626.3 [M-PF₆]⁺

Then, using a mononuclear complex [Pt(4,4'-dmbpy)(3-ᵗBupzH)₂](PF₆)₂, which is an intermediate material, a metal complex [Pt₂(4,4'-dmbpy)₂(3-ᵗBupz)₂(3-ᵗBupzH)₂](PF₆)₂ was synthesized. To be specific, KOH (2 equivalents) was added to a solution (10 mL) of [Pt(4,4'-dmbpy)(3-$^t$BupzH)$_2$](PF$_6$)$_2$ (37 mg, 0.04 mmol) in methanol, and the mixture was stirred at room temperature for 3 hr. The reaction solution changed from white-yellow to yellow. This solution was concentrated to dryness. The obtained yellow solid was dissolved in acetonitrile, and unreacted KOH was filtered off. The yellow filtrate was concentrated to dryness. The obtained solid was dissolved in dichloromethane, and hexane was added to this solution. The precipitated yellow solid was collected, washed with hexane and dried under reduced pressure. The yield was 12.8 mg, 42%. This reaction can be shown by the following chemical reaction formula.

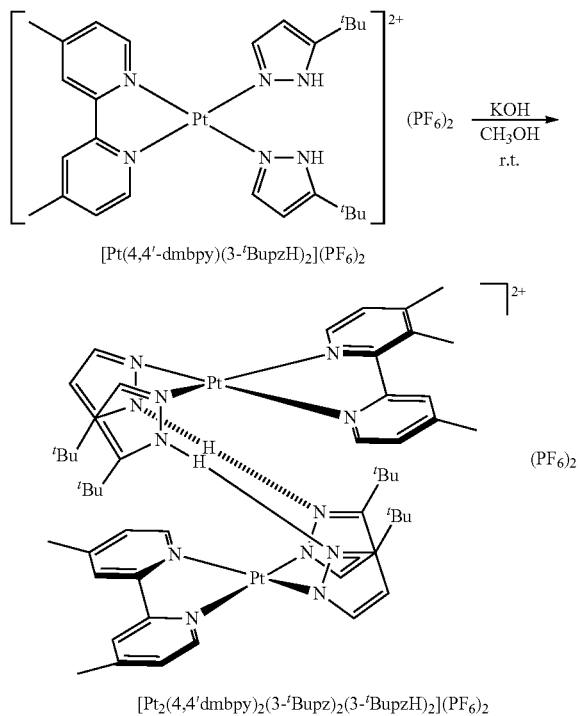

This metal complex exhibited yellow emission under irradiation of UV light (365 nm). This metal complex was readily soluble in acetone, methanol, ethanol, dichloromethane, chloroform and DMF, soluble in THF, benzene, diethyl ether, acetonitrile, DMSO and toluene, and insoluble in water and hexane.

Furthermore, the product was identified by IR and $^1$H NMR spectra.

The results of identification by IR spectrum are as follows.
IR(KBr): 3347 (w), 2958 (s), 2360 (m), 2342 (m), 1624 (s), 1491 (m), 1418 (w), 1236 (s), 833 (s), 560 (s)

The results of identification by $^1$H NMR spectrum are as shown in the following Table 21. Each item in Table 21 is as defined in Table 1.

TABLE 21

$^1$H NMR data of [Pt$_2$(4,4'-dmbpy)$_2$(3-$^t$Bupz)$_2$(3-$^t$BupzH)$_2$](PF$_6$)$_2$ (in CDCl$_3$, TMS, 300 MHz)

| δ (ppm) | Shape(J/Hz) | Int. | Assign. |
| --- | --- | --- | --- |
| 8.95 | d (6.0) | 1H | H6 of 4,4'-dmbpy |
| 7.77 | s | 1H | H3 of 4,4'-dmbpy |
| 7.24 | s | 1H | H5 of 4,4'-dmbpy |
| 6.99 | d (1.9) | 1H | H5 of 3-$^t$Bupz |
| 5.99 | d (1.9) | 1H | H4 of 3-$^t$Bupz |
| 2.48 | s | 3H | Me of 4,4'-dmbpy |
| 1.38 | s | 9H | $^t$Bu of 3-$^t$Bupz |

Furthermore, mass spectrometry was performed by the FAB-MS method. The results are as follows.

FAB-MS: m/z=1251.6 [M-PF$_6$]$^+$

Figure 23:
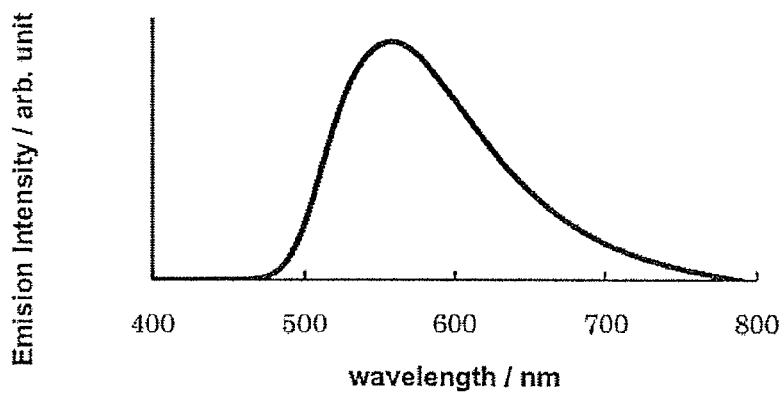
FIG. 23 shows an emission spectrum of [Pt$_2$(4,4'-dmbpy)$_2$(3-$^t$Bupz)$_2$(3-$^t$BupzH)$_2$](PF$_6$)$_2$ in a solid state (measurement temperature: 298K).

The emission properties of the metal complex [Pt$_2$(4,4'-dmbpy)$_2$(3-$^t$Bupz)$_2$(3-$^t$BupzH)$_2$](PF$_6$)$_2$ are now explained. The emission spectrum of the metal complex in a solid state was measured. The emission spectrum is shown in FIG. 23.

When [Pt$_2$(4,4'-dmbpy)$_2$(3-$^t$Bupz)$_2$(3-$^t$BupzH)$_2$](PF$_6$)$_2$ in a solid state was excited with 355 nm UV light at 298K, a broad spectrum showing an emission maximum at 557 nm was obtained. The emission quantum yield (Φ) in a solid state was 0.13.

Moreover, the emission decay curve of this metal complex in a solid state was measured, and analyzed using a biexponential function (I(t)=A$_1$exp(-t/τ$_1$)+A$_2$exp(-t/τ$_2$)) to give the values of τ$_1$=0.29 μs, A$_1$=0.61, τ$_2$=1.13 μs and A$_2$=0.39 (measurement temperature: 298K). The emission lifetime of this metal complex is comparatively long and the emission is considered to occur from a triplet excited state (i.e., phosphorescence).

Example 13

[Pt$_2$Ag$_2$(4,4-dmbpy)$_2$(3-$^t$Bupz)$_4$](PF$_6$)$_2$, which is one kind of the metal complex of the present invention, was synthesized. This metal complex has a constitution wherein, in the above-mentioned formula (C1), M$^{II}$ is Pt$^{II}$, M$^I$ is Ag$^I$, L$_C$ is 4,4'-dmbpy, L$_B$ is 3-$^t$Bupz, and the counter anion is PF$_6$$^-$.

First, a mononuclear complex [Pt(4,4'-dmbpy)(3-$^t$BupzH)$_2$](PF$_6$)$_2$ was synthesized as an intermediate material in the same manner as in the method explained in Example 12.

Then, using the mononuclear complex [Pt(4,4'-dmbpy)(3-$^t$BupzH)$_2$](PF$_6$)$_2$r which is an intermediate material, a metal complex [Pt$_2$Ag$_2$(4,4'-dmbpy)$_2$(3-$^t$Bupz)$_4$](PF$_6$)$_2$ was synthesized. To be specific, AgBF$_4$ (9.7 mg, 0.05 mmol) and triethylamine (20 μL, 0.12 mmol) were added to a solution (10 mL) of [Pt(4,4'-dmbpy)(3-$^t$BupzH)$_2$](PF$_6$)$_2$ (40.1 mg, 0.04 mmol) in acetonitrile, and the mixture was stirred under shading at room temperature for 3 hr. At this time, the yellow solution changed to a yellow suspension. The yellow solid precipitated by the reaction was collected by filtration, washed with hexane and dried under reduced pressure. The yield was 9.6 mg, 23%. In addition, when the filtrate was concentrated and methanol was added, a yellow solid precipitated. The yellow solid precipitated with methanol was collected by filtration, washed with methanol and dried under reduced pressure. The yield was 18.2 mg, 43%. This reaction can be shown by the following chemical reaction formula.

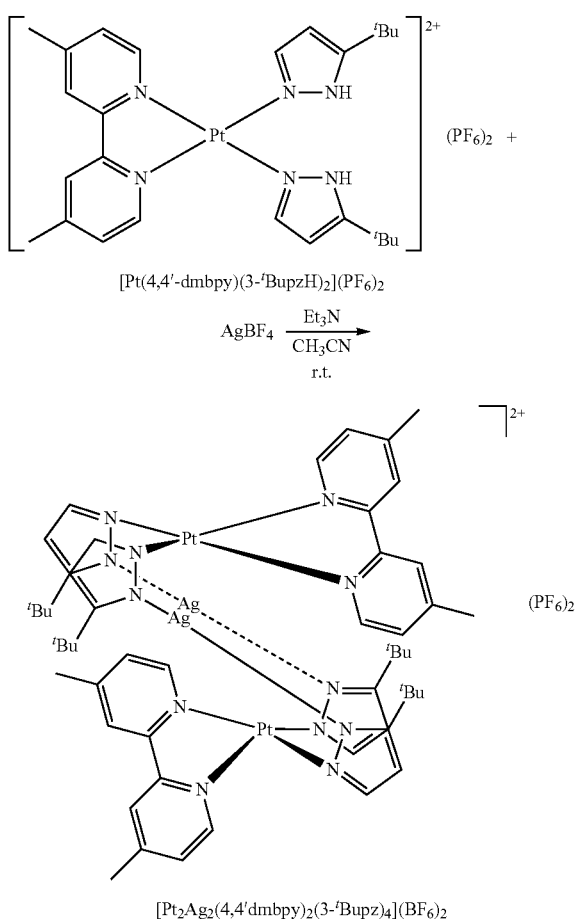

[Pt(4,4'-dmbpy)(3-'BupzH)₂](PF₆)₂

AgBF₄ →(Et₃N / CH₃CN, r.t.)

[Pt₂Ag₂(4,4'dmbpy)₂(3-'Bupz)₄](BF₆)₂

The solid precipitated by the reaction exhibited yellow emission under irradiation of UV light (365 nm). On the other hand, the solid precipitated with methanol exhibited blue emission under irradiation of UV light (365 nm). The solid exhibiting yellow emission and that exhibiting blue emission gave identical ¹H NMR spectra and ESI-MS data as mentioned below. In addition, the solid exhibiting yellow emission and that exhibiting blue emission both yielded, by recrystallization, yellow crystals exhibiting blue emission. From these data, it is considered that the metal complex contained in the solid exhibiting yellow emission and that contained in the solid exhibiting blue emission are not isomers but the same metal complex, and these solids show different luminescent colors according to the difference in the packing of the metal complexes.

The solid exhibiting yellow emission was readily soluble in dichloromethane, chloroform, acetonitrile and DMSO, slightly soluble in methanol, ethanol and diethylether, and insoluble in hexane. On the other hand, the solid exhibiting blue emission was easily soluble in dichloromethane, chloroform, acetonitrile and DMSO, slightly soluble in diethylether, and insoluble in methanol, ethanol and hexane.

The results of identification by IR spectrum of the crystal exhibiting blue emission obtained by recrystallization, and those by ¹H NMR spectra of the solid exhibiting yellow emission and the solid exhibiting blue emission are as shown below. Each item in Table 22 is as defined in Table 1.

IR(KBr): 3471 (w), 2953 (s), 2359 (w), 2341 (w), 1620 (s), 1491 (s), 1329 (s), 1248 (s), 1081 (s), 840 (s), 770 (m), 521 (s), 501 (m)

TABLE 22

¹H NMR data of [Pt₂Ag₂(4-4' dmbpy)₂(3-'Bupz)₄](PF₆)₂ (in CD₃CN, TMS, 300 MHz)

| δ (ppm) | Shape(J/Hz) | Int. | Assign. |
|---|---|---|---|
| 7.98 | s | 1H | H6 of 4-4' dmbpy |
| 7.20 | s | 1H | H3 of 4-4' dmbpy |
| 6.51 | t (1.8) | 1H | H5 of 4-4' dmbpy |
| 6.05 | s | 1H | H5 of 3-'Bupz |
| 5.90 | t (2.5) | 1H | H4 of 3-'Bupz |
| 2.50 | s | 3H | Me of 4-4' dmbpy |
| 1.39 | s | 9H | 'Bu of 3-'BupzH |

Furthermore, mass spectrometry was performed by the ESI-MS method. The results are as follows.

ESI-MS: 1611.6 [M-PF₆]⁺

Using the yellow solid exhibiting blue emission, recrystallization from dichloromethane/ethanol was performed to give yellow crystals. Using the crystals, the molecular structure was determined by single crystal X-ray structural analysis. The crystallographic data are shown in Table 23. Here, each item in Table 23 is as defined in Table 6.

TABLE 23

Crystallographic data for [Pt₂Ag₂(4,4'-dmbpy)₂(3-'Bupz)₄](PF₆)₂

| | |
|---|---|
| Empirical Formula | C₅₂H₆₈Ag₂F₁₂N₁₂P₂Pt₂ |
| Fw | 1757.03 |
| T, K | 93 |
| λ, Å | 0.71075 |
| Cryst Syst | monoclinic |
| Space Group | P2₁/c (# 14) |
| a, Å | 13.001(3) |
| b, Å | 16.884(4) |
| c, Å | 14.556(3) |
| β, deg | 112.524(3) |
| V, Å³ | 2951.5(11) |
| Z | 2 |
| ρ$_{calcd}$, g cm⁻³ | 1.977 |
| μ(Mo Kα), cm⁻¹ | 54.973 |
| No. of Reflections Measured | Unique: 6751 (R$_{int}$ = 0.0489) |
| Residuals: R; Rw | 0.0517; 0.1084 |
| Residuals: R1 | 0.0420 |
| GOF | 1.065 |

Figure 24:
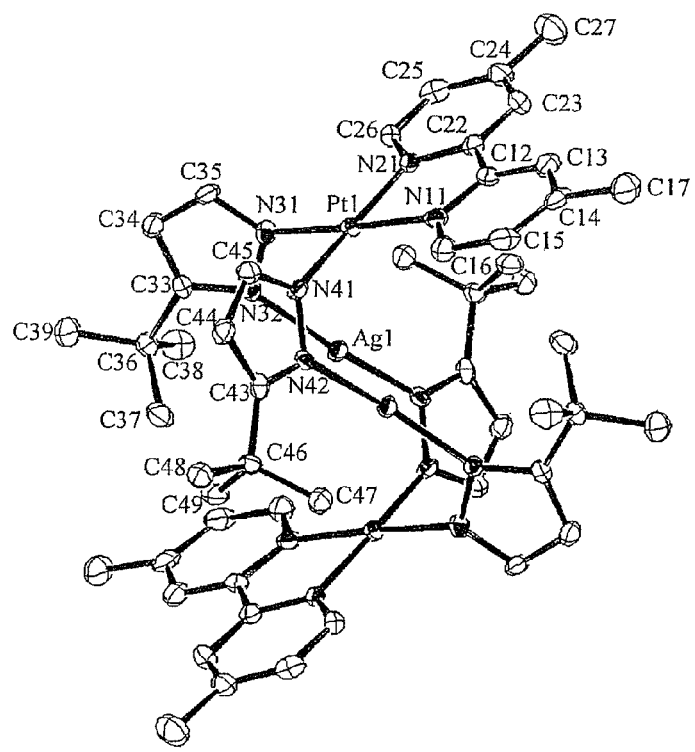
FIG. 24 is an ORTEP diagram showing the structure of a cation in [Pt$_2$Ag$_2$(4,4'-dmbpy)$_2$(3-$^t$Bupz)$_4$](PF$_6$)$_2$ exhibiting blue emission.

In addition, the structure of cation in the crystal exhibiting blue emission is shown in the ORTEP diagram of FIG. 24. As shown in FIG. 24, two Pt atoms and two Ag atoms are contained in this cation. A crystallographically imposed center of symmetry is located at the midpoint between Ag . . . Ag, and a half of the atoms in the crystals is independent. 4,4'-Dimethyl-2,2'-bipyridine (4,4'-dmbpy) coordinates as a bidentate chelating ligand to each Pt atom, and two 3-t-butylpyrazolato ligands (3-'Bupz) coordinate with N atom located farther from t-butyl group to the residual coordination site. Each Pt atom forms a {(4,4'-dmbpy)Pt(3-'Bupz)₂} unit, and two 3-'Bupz ligands of each unit coordinate to different Ag atoms, whereby a 12-membered ring containing two Pt atoms and two Ag atoms is formed. In [Pt₂Ag₂(4,4'-dmbpy)₂(3-'Bupz)₄](PF₆)₂, the Pt . . . Pt distance is 6.3489(11) Å.

The Pt . . . Ag distances are 3.5265(8) Å and 3.5260(8) Å, and the Ag . . . Ag distance is 3.0705(8) Å. The Pt—N distances are within the range of 1.994(5) Å-2.016(5) Å, and the Ag—N distances are 2.096(6) Å and 2.097(6) Å.

Figure 25:
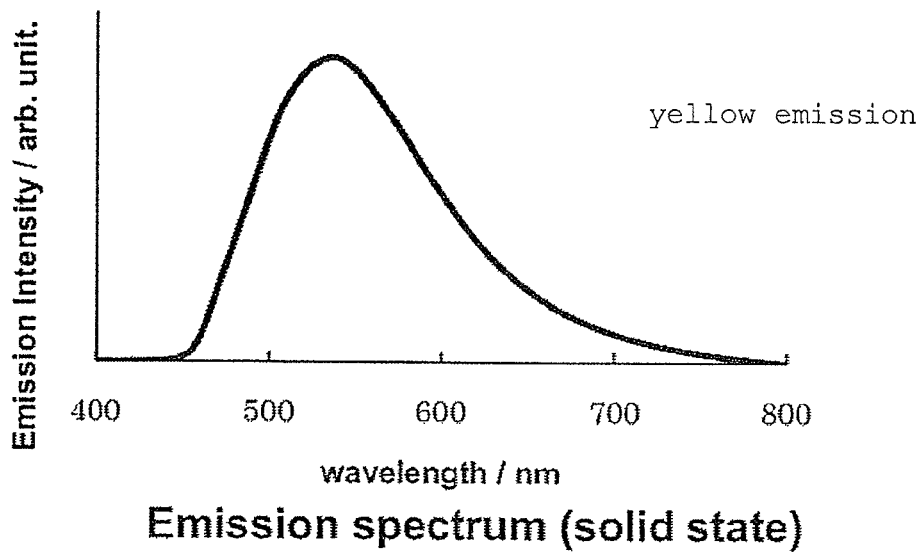
FIG. 25 shows an emission spectrum of [Pt$_2$Ag$_2$(4,4'-dmbpy)$_2$(3-$^t$Bupz)$_4$](PF$_6$)$_2$ in a solid state and exhibiting yellow emission (measurement temperature: 298K).
Figure 26:
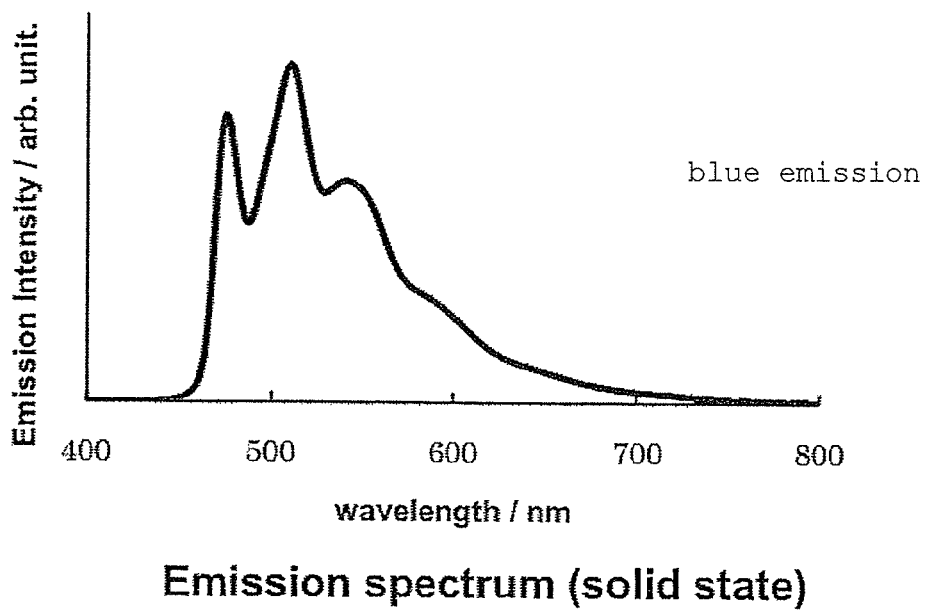
FIG. 26 shows an emission spectrum of [Pt$_2$Ag$_2$(4,4'-dmbpy)$_2$(3-$^t$Bupz)$_4$](PF$_6$)$_2$ in a solid state and exhibiting blue emission (measurement temperature: 298K).

The emission properties of the metal complex [Pt₂Ag₂(4,4'-dmbpy)₂(3-'Bupz)₄](PF₆)₂ are now explained. The emission spectrum of the metal complex in a solid state was measured. The emission spectrum of the solid exhibiting yellow emission is shown in FIG. 25 and the emission spectrum of the crystal exhibiting blue emission is shown in FIG. 26.

When the solid exhibiting yellow emission was excited with 355 nm UV light at 298K, the spectrum with an emission maximum wavelength at 536 nm was obtained. On the other hand, when the crystal exhibiting blue emission was excited with 355 nm UV light at 298K, a spectrum with a vibrational structure having emission maxima at 476 nm, 510 nm and 543 nm was obtained. The emission quantum yield (Φ) of the crystal exhibiting blue emission in a solid state was 0.53.

Moreover, the emission decay curve of the crystal exhibiting blue emission in a solid state was measured, and analyzed using a biexponential function (I(t)=$A_1$exp(-t/$\tau_1$)+$A_2$exp(-t/$\tau_2$)) to give the values of $\tau_1$=0.26 μs, $A_1$=0.52, $\tau_2$=0.73 μs and $A_2$=0.48 (measurement temperature: 298K). The emission lifetime of this metal complex is comparatively long and the emission is considered to occur from a triplet excited state (i.e., phosphorescence).

INDUSTRIAL APPLICABILITY

The metal complex of the present invention is a material useful for the production of a light emitting device, a display device, and the like.

This application is based on patent application Nos. 2010-211191 and 2011-53216 filed in Japan, the contents of which are encompassed in full herein.

EXPLANATION OF SYMBOLS 1 substrate
2 anode
3 hole injection layer
4 hole transport layer
5 light emitting layer
6 electron transport layer
7 electron injection layer
8 cathode

The invention claimed is:

1. A metal complex containing a cation represented by the formula (C1)

in the formula (C1), $M^{II}$ is $Pt^{II}$ or $Pd^{II}$,
$M^I$ is $H^+$, $Au^I$, $Ag^I$, $Cu^I$, $Hg^I$, $Tl^I$ or $Pb^I$,
$L_C$ is a compound represented by any of the formula ($L_C$-1)-the formula ($L_C$-5), and
$L_B$ is a monovalent anion represented by the formula ($L_B$-1),

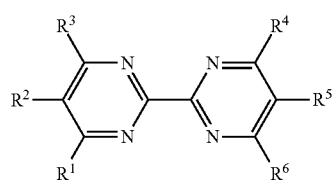

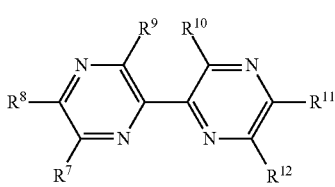

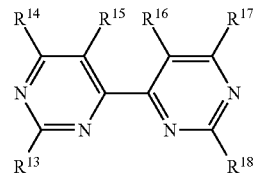

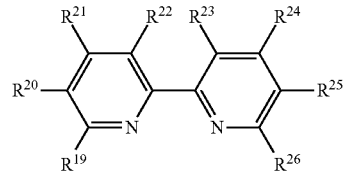

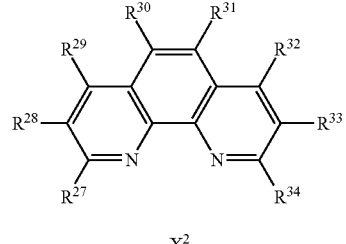

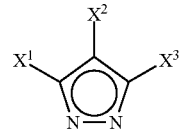

in the formula ($L_C$-1)-the formula ($L_C$-5), $R^1$-$R^{34}$ are each independently a hydrogen atom, a halogen atom, an alkyl group optionally having substituent(s), or an aryl group optionally having substituent(s), or one or plural sets of the adjacent groups from $R^1$-$R^{34}$ form a hydrocarbon ring optionally having substituent(s) or a heterocyclic ring optionally having substituent(s), in the formula ($L_B$-1), $X^1$ is an alkyl group optionally having substituent(s), and $X^2$ and $X^3$ are each independently a hydrogen atom, a halogen atom, an alkyl group optionally having substituent(s), or an aryl group optionally having substituent(s).

2. The metal complex according to claim 1, which is represented by the formula (C2)

in the formula (C2), $M^{II}$, $M^I$, $L_C$ and $L_B$ are as defined above.

3. The metal complex according to claim 1, wherein $M^{II}$ is $Pt^{II}$, $M^I$ is $H^+$, $Au^I$, $Ag^I$ or $Cu^I$, $L_C$ is 2,2'-bipyrimidine or 2,2'-bipyridine, and $L_B$ is a monovalent anion obtained by dissociation of a proton from 3-t-butylpyrazole.

4. The metal complex according to claim 1, wherein $M^{II}$ is $Pt^{II}$, $M^I$ is $H^+$ or $Ag^I$, $L_C$ is 4,4'-dimethyl-2,2'-bipyridine or 5,5'-dimethyl-2,2'-bipyridine, and $L_B$ is a monovalent anion obtained by dissociation of a proton from 3-t-butylpyrazole.

5. A light emitting device having a light emitting layer comprising the metal complex according to claim 1.

6. A display device provided with the light emitting device according to claim 5.

7. The metal complex according to claim 2, wherein $M^{II}$ is $Pt^{II}$, $M^I$ is $H^+$, $Au^I$, $Ag^I$ or $Cu^I$, $L_C$ is 2,2'-bipyrimidine or 2,2'-bipyridine, and $L_B$ is a monovalent anion obtained by dissociation of a proton from 3-t-butylpyrazole.

8. The metal complex according to claim 2, wherein $M^{II}$ is $Pt^{II}$, $M^{I}$ is $H^+$ or $Ag^{I}$, $L_C$ is 4,4'-dimethyl-2,2'-bipyridine or 5,5'-dimethyl-2,2'-bipyridine, and $L_B$ is a monovalent anion obtained by dissociation of a proton from 3-t-butylpyrazole.

9. A light emitting device having a light emitting layer comprising the metal complex according to claim 2.

10. A light emitting device having a light emitting layer comprising the metal complex according to claim 3.

11. A light emitting device having a light emitting layer comprising the metal complex according to claim 4.

12. A light emitting device having a light emitting layer comprising the metal complex according to claim 7.

13. A light emitting device having a light emitting layer comprising the metal complex according to claim 8.

14. A display device provided with the light emitting device according to claim 9.

15. A display device provided with the light emitting device according to claim 10.

16. A display device provided with the light emitting device according to claim 11.

17. A display device provided with the light emitting device according to claim 12.

18. A display device provided with the light emitting device according to claim 13.

* * * * *